(12) United States Patent
Lee et al.

(10) Patent No.: US 11,898,188 B2
(45) Date of Patent: Feb. 13, 2024

(54) MUTANT MICROORGANISM HAVING ABILITY TO PRODUCE 1,3-PROPANEDIOL, AND METHOD FOR PREPARING 1,3-PDO BY USING SAME

(71) Applicants: KOREA ADVANCED INSTITUTE OF SCIENCE AND TECHNOLOGY, Daejeon (KR); HANWHA SOLUTIONS CORPORATION, Seoul (KR)

(72) Inventors: Sang Yup Lee, Daejeon (KR); Jae Sung Cho, Daejeon (KR); Je Woong Kim, Daejeon (KR); Yoo Sung Ko, Daejeon (KR); Cindy Pricilia Surya Prabowo, Daejeon (KR); Taehee Han, Daejeon (KR); Euiduk Kim, Daejeon (KR); Jae Won Choi, Daejeon (KR); Changhee Cho, Daejeon (KR); Jun Kyu Lee, Daejeon (KR)

(73) Assignees: HANWHA SOLUTIONS CORPORATION, Seoul (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 16/962,213

(22) PCT Filed: Jan. 15, 2019

(86) PCT No.: PCT/KR2019/000571
§ 371 (c)(1),
(2) Date: Jul. 14, 2020

(87) PCT Pub. No.: WO2019/143089
PCT Pub. Date: Jul. 25, 2019

(65) Prior Publication Data
US 2021/0062232 A1    Mar. 4, 2021

(30) Foreign Application Priority Data

Jan. 16, 2018    (KR) .................. 10-2018-0005451

(51) Int. Cl.
| C12P 7/18 | (2006.01) |
| C12N 9/04 | (2006.01) |
| C12N 9/12 | (2006.01) |
| C12N 9/88 | (2006.01) |
| C12N 15/77 | (2006.01) |
| C12N 1/21 | (2006.01) |

(52) U.S. Cl.
CPC .............. *C12P 7/18* (2013.01); *C12N 9/0006* (2013.01); *C12N 9/1205* (2013.01); *C12N 9/88* (2013.01); *C12N 15/77* (2013.01); *C12Y 101/01006* (2013.01); *C12Y 101/01202* (2013.01); *C12Y 207/0103* (2013.01); *C12Y 402/0103* (2013.01)

(58) Field of Classification Search
None
See application file for complete search history.

(56) References Cited

U.S. PATENT DOCUMENTS

| 8,236,994 B2 | 8/2012 | Soucaille |
| 2010/0129884 A1* | 5/2010 | Cho .................... C12N 9/1205 435/142 |
| 2012/0301935 A1 | 11/2012 | Yu et al. |

FOREIGN PATENT DOCUMENTS

| KR | 1008308260000 B1 | 5/2008 |
| KR | 1011460800000 B1 | 5/2012 |
| KR | 1157376 B1 * | 6/2012 |
| KR | 1020130022691 A | 3/2013 |
| KR | 1020140145397 A | 12/2014 |
| WO | 2016200239 A1 | 12/2016 |

OTHER PUBLICATIONS

Yang et al., Pathway Construction in Corynebacterium glutamicum and Strain Engineering To Produce Rare Sugars from Glycerol, J. Agric. Food Chem. 64, 2016, 9479-9505. (Year: 2016).*
Tobimatsu et al., Identification and Expression of the Genes Encoding a Reactivating Factor for Adenosylcobalamin-Dependent Glycerol Dehydratase, J. Bacteriol. 181, 1999, 4110-13. (Year: 1999).*
Eikmanns, B. J., et al., "A family of Corynebacterium glutamicum/ *Escherichia coli* shuttle vectors for cloning, controlled gene expression, and promoter probing", "Gene", 1991, pp. 93-98, vol. 102.
Huang, J., et al., "Cofactor Recycling for Co-Production of 1,3-propanediol and Glutamate by Metabolically Engineered Corynebacterium Glutamicum", "Nature/ Scientific Reports", 2017, pp. 1-10.
Lee, C.S., et al., "A Review: Conversion of Bioglycerol into 1,3-propanediol via Biological and Chemical Method", "Renewable and Sustainable Energy Reviews", 2015, pp. 963-972, vol. 42.
Neumann, E., et al., "Gene Transfer into Mouse Lyoma Cells by Electroporation in High Electric Fields", "The EMBO Journal", Jun. 30, 1982, pp. 841-845, vol. 1, No. 7.
Rittmann, D., et al., "Engineering of a Glycerol Utilization Pathway for Amino Acid Production by Corynebacterium Glutamicum", "Applied and Environmental Microbiology", Jan. 2008, pp. 6216-6222, vol. 74, No. 20.

(Continued)

*Primary Examiner* — Todd M Epstein
(74) *Attorney, Agent, or Firm* — HULTQUIST, PLLC; Steven J. Hultquist

(57) ABSTRACT

The present disclosure relates to a mutant microorganism in which a glycerol catabolic pathway and a 1,3-PDO biosynthetic pathway are introduced into a microorganism incapable of using glycerol as a carbon source, and a method of producing 1,3-PDO using the same. According to the present disclosure, it is possible to produce 1,3-PDO while growing a mutant microorganism having 1,3-PDO production ability by using the inexpensive raw material glycerol as a single carbon source. Thus, the present disclosure is useful for the economical production of 1,3-PDO.

2 Claims, 17 Drawing Sheets
Specification includes a Sequence Listing.

(56) References Cited

OTHER PUBLICATIONS

Yim, S.S., et al., "Isolation of Fully Synthetic Promoters for High-Level Gene Expression in Corynebacterium Glutamicum", "Biotechnology and Bioengineering", 2013, pp. 1-37.

Przystalowska, H., et al., "1, 3-Propanediol production by new recombinant *Eschericia coli* containing genes from pathogenic bacteria", Microbiological Research, 2015, pp. 1-7, vol. 121, Publisher: Elsevier.

Huang, J., et al., "Cofactor recycling for co-production of 1,3-propanediol and glutamate by metabolically engineered Corynebacterium glutamicum", Scientific Reports, 2017, Page(s) DOI: 10.1038/srep42246, vol. 7, No. 42246, Publisher: www.nature.com/scientificreports.

Nakamura, C.E., et al., "Metabolic engineering for the microbial production of 1,3-propanediol", Current Opinion in Biotechnology, 2003, vol. 14, pp. 454-459.

Search Report Issued in Chinese Patent Application No. 201980016833.8 dated Aug. 31, 2023.

Office Action Issued in Chinese Patent Application No. 201980016833.8 dated Aug. 31, 2023.

English Translation of Office Action Issued in Chinese Patent Application No. 201980016833.8 dated Aug. 31, 2023.

Hong, E., et al., "Improved 1,3-propanediol Production by *Escherichia coli* from Glycerol Due to Co-expression of Glycerol Dehydratase Reactivation Factors and Succinate Addition", Biotechnology and Bioprocess Engineering, 2015, pp. 849-855; DOI 10.1007/s12257-015-0293-8, vol. 20, Publisher: Springer.

Zhou, W-G, et al., "Studies on the production of 1,3-propanediol by constructing gene engineering bacteria", Journal of Guangxi University, 2003, pp. 305-308, vol. 28, No. 4, Publisher: Nat Sci Ed.

"English Translation: Studies on the production of 1,3-propanediol by constructing gene engineering bacteria", Journal of Guangxi University, 2003, pp. 305-308, vol. 28, No. 4, Publisher: Nat Sci Ed.

\* cited by examiner

SEQUENCE LISTING

<160> NUMBER OF SEQ ID NOS: 23

<210> SEQ ID NO 1
<211> LENGTH: 47
<212> TYPE: DNA
<213> ORGANISM: Artificial Sequence
<220> FEATURE:
<223> OTHER INFORMATION: Synthetic construct

<400> SEQUENCE: 1
ttggttggta ggagtagcat gggatccatg agtcaaacat caacctt                47

<210> SEQ ID NO 2
<211> LENGTH: 40
<212> TYPE: DNA
<213> ORGANISM: Artificial Sequence
<220> FEATURE:
<223> OTHER INFORMATION: Synthetic construct

<400> SEQUENCE: 2
gtttccatct atatctcctt ttattcgtcg tgttcttccc                         40

<210> SEQ ID NO 3
<211> LENGTH: 32
<212> TYPE: DNA
<213> ORGANISM: Artificial Sequence
<220> FEATURE:
<223> OTHER INFORMATION: Synthetic construct

<400> SEQUENCE: 3
aaggagatat agatggaaac caaagatctg at                                 32

<210> SEQ ID NO 4
<211> LENGTH: 50
<212> TYPE: DNA
<213> ORGANISM: Artificial Sequence
<220> FEATURE:
<223> OTHER INFORMATION: Synthetic construct

<400> SEQUENCE: 4
taattataat ggccggctgg gcctctagag ttacgacgcc agcgataacc               50

<210> SEQ ID NO 5
<211> LENGTH: 30
<212> TYPE: DNA
<213> ORGANISM: Artificial Sequence
<220> FEATURE:
<223> OTHER INFORMATION: Synthetic construct

<400> SEQUENCE: 5
tctagaggcc cagccggcca ttataattag          30

<210> SEQ ID NO 6
<211> LENGTH: 30
<212> TYPE: DNA
<213> ORGANISM: Artificial Sequence
<220> FEATURE:
<223> OTHER INFORMATION: Synthetic construct

<400> SEQUENCE: 6
ggatcccatg ctactcctac caaccaaggt          30

<210> SEQ ID NO 7
<211> LENGTH: 42
<212> TYPE: DNA
<213> ORGANISM: Artificial Sequence
<220> FEATURE:
<223> OTHER INFORMATION: Synthetic construct

<400> SEQUENCE: 7
acaatttcac acaggaaaca gaattcatga aaagatcaaa ac          42

<210> SEQ ID NO 8
<211> LENGTH: 43
<212> TYPE: DNA
<213> ORGANISM: Artificial Sequence
<220> FEATURE:
<223> OTHER INFORMATION: Synthetic construct

<400> SEQUENCE: 8
aaaacagcca agcttggctg cagtcagttt ctctcactta acg          43

<210> SEQ ID NO 9
<211> LENGTH: 48
<212> TYPE: DNA
<213> ORGANISM: Artificial Sequence
<220> FEATURE:
<223> OTHER INFORMATION: Synthetic construct

<400> SEQUENCE: 9
acaatttcac acaggaaaca gaattcatga gatcgaaaag atttgaag          48

<210> SEQ ID NO 10
<211> LENGTH: 46
<212> TYPE: DNA
<213> ORGANISM: Artificial Sequence
<220> FEATURE:
<223> OTHER INFORMATION: Synthetic construct

<400> SEQUENCE: 10
aaaacagcca agcttggctg cagttaagca tggcgatccc gaaatg          46

<210> SEQ ID NO 11
<211> LENGTH: 41
<212> TYPE: DNA
<213> ORGANISM: Artificial Sequence
<220> FEATURE:
<223> OTHER INFORMATION: Synthetic construct

<400> SEQUENCE: 11
tggatgatgg ggcgattcag gttgacaatt aatcatcggc t          41

<210> SEQ ID NO 12
<211> LENGTH: 44
<212> TYPE: DNA
<213> ORGANISM: Artificial Sequence
<220> FEATURE:
<223> OTHER INFORMATION: Synthetic construct

<400> SEQUENCE: 12
aaggtgttgc tgactcatac caggttagcg ggcggcttcg tata            44

<210> SEQ ID NO 13
<211> LENGTH: 44
<212> TYPE: DNA
<213> ORGANISM: Artificial Sequence
<220> FEATURE:
<223> OTHER INFORMATION: Synthetic construct

<400> SEQUENCE: 13
aaggtgttgc tgactcatac caggttagcg tgcagcctcg taaa            44

<210> SEQ ID NO 14
<211> LENGTH: 44
<212> TYPE: DNA
<213> ORGANISM: Artificial Sequence
<220> FEATURE:
<223> OTHER INFORMATION: Synthetic construct

<400> SEQUENCE: 14
aaggtgttgc tgactcatac caggtcagaa tgcctggcgg aaaa            44

<210> SEQ ID NO 15
<211> LENGTH: 32
<212> TYPE: DNA
<213> ORGANISM: Artificial Sequence
<220> FEATURE:
<223> OTHER INFORMATION: Synthetic construct

<400> SEQUENCE: 15
ttccaatgat gagcactttt ttgacaatta at            32

<210> SEQ ID NO 16
<211> LENGTH: 43
<212> TYPE: DNA
<213> ORGANISM: Artificial Sequence
<220> FEATURE:
<223> OTHER INFORMATION: Synthetic construct

<400> SEQUENCE: 16
gcgccacata gcagaacttt ttagcgggcg gcttcgtata tac            43

<210> SEQ ID NO 17
<211> LENGTH: 43
<212> TYPE: DNA
<213> ORGANISM: Artificial Sequence
<220> FEATURE:
<223> OTHER INFORMATION: Synthetic construct

<400> SEQUENCE: 17
gcgccacata gcagaacttt ttagcgtgca gcctcgtaaa tac            43

<210> SEQ ID NO 18
<211> LENGTH: 41
<212> TYPE: DNA
<213> ORGANISM: Artificial Sequence
<220> FEATURE:
<223> OTHER INFORMATION: Synthetic construct

<400> SEQUENCE: 18
gcgccacata gcagaacttt tcagaatgcc tggcggaaaa t         41

<210> SEQ ID NO 19
<211> LENGTH: 2405
<212> TYPE: DNA
<213> ORGANISM: Artificial Sequence
<220> FEATURE:
<223> OTHER INFORMATION: Synthetic construct

<400> SEQUENCE: 19

| | |
|---|---|
| atgagtcaaa catcaacctt gaaaggccag tgcattgctg aattcctcgg taccggttg | 60 |
| ttgattttct tcggtgtggg ttgcgttgca gcactaaaag tcgctggtgc gtcttttggt | 120 |
| cagtgggaaa tcagtgtcat ttggggactg ggggtggcaa tggccatcta cctgaccgca | 180 |
| ggggtttccg cgcgcatct taatcccgct gttaccattg cattgtggct gttttgcctgt | 240 |
| ttcgacaagc gcaaagttat tccttttatc gtttcacaag ttgccggcgc tttctgtgct | 300 |
| gcggctttag tttacgggct ttactacaat ttatttttcg acttcgagca gactcatcac | 360 |
| attgttcgcg gcagcgttga aagtgttgat ctggctggca cttctctac ttaccctaat | 420 |
| cctcatatca attttgtgca ggctttcgca gttgagatgg tgattaccgc tattctgatg | 480 |
| gggctgatcc tggcgttaac ggacgatggc aacggtgtac cacgcggccc tttggctccc | 540 |
| ttgctgattg gtctactgat tgcggtcatt ggcgcatcta tgggcccatt gacaggtttt | 600 |
| gccatgaacc cagcgcgtga cttcggtccg aaagtctttg cctggctggc gggctggggc | 660 |
| aatgtcgcct ttaccggcgg cagagacatt ccttacttcc tggtgccgct tttcggccct | 720 |
| atcgttggcg cgattgtagg tgcatttgcc taccgcaaac tgattggtcg ccatttgcct | 780 |
| tgcgatatct gtgttgtgga agaaaaggaa accacaactc cttcagaaca aaaagcttcg | 840 |
| ctgtaatatg actacgggac aattaaacat gactgaaaaa aaatatatcg ttgcgcatga | 900 |
| ctgaaaaaaa atatatcgtt gcgctcgacc agggcaccac cagctcccgc gcggtcgtaa | 960 |
| tggatcacga tgccaatatc attagcgtgt cgcagcgcga atttgagcaa atctacccaa | 1020 |
| aaccaggttg ggtagaacac gacccaatgg aaatctgggc cacccaaagc tccacgctgg | 1080 |
| tagaagtgct ggcgaaagcc gatatcagtt ccgatcaaat tgcagctatc ggtattacga | 1140 |
| accagcgtga aaccactatt gtctgggaaa agaaaccgg caagcctatc tataacgcca | 1200 |
| ttgtctggca gtgccgtcgt accgcagaaa tctgcgagca tttaaaacgt gacggtttag | 1260 |
| aagattatat ccgcagcaat accggtctgg tgattgaccc gtactttcct ggcaccaaag | 1320 |
| tgaagtggat cctcgaccat gtggaaggct ctcgcgagcg tgcacgtcgt ggtgaattgc | 1380 |
| tgtttggtac ggttgatacg tggcttatct ggaaaatgac tcaggccgt gtccatgtga | 1440 |
| ccgattacac caacgcctct cgtaccatgt tgttcaacat ccatacccctg gactgggacg | 1500 |
| acaaaatgct ggaagtgctg gatattccgc gcgagatgct gccagaagtg cgtcgttctt | 1560 |
| ccgaagtata cggtcagact aacattggcg gcaaaggcgg cacgcgtatt ccaatctccg | 1620 |
| ggatcgccgg tgaccagcag gccgcgctgt ttggtcagtt gtgcgtgaaa gaagggatgg | 1680 |
| cgaagaacac ctatggcact ggctgctta tgctgatgaa cactggcgag aaagcggtga | 1740 |
| aatcagaaaa cggcctgctg accaccatcg cctgcggccc gactggcgaa gtgaactatg | 1800 |
| cgttggaagg tgcggtgttt atggcaggcg catccattca gtggctgcgc gatgaaatga | 1860 |
| agttgattaa cgacgcctac gattccgaat atttcgccac caaagtgcaa aacaccaatg | 1920 |

-continued

```
gtgtgtatgt ggttccggca tttaccgggc tgggtgcgcc gtactgggac ccgtatgcgc    1980
gcggggcgat tttcggtctg actcgtgggg tgaacgctaa ccacattata cgcgcgacgc    2040
tggagtctat tgcttatcag acgcgtgacg tgctggaagc gatgcaggcc gactctggta    2100
tccgtctgca cgccctgcgc gtggatggtg gcgcagtagc aaacaatttc ctgatgcagt    2160
tccagtccga tattctcggc acccgcgttg agcgcccgga agtgcgcgaa gtcaccgcat    2220
tgggtgcggc ctatctcgca ggcctggcgg ttggcttctg gcagaacctc gacgagctgc    2280
aagagaaagc ggtgattgag cgcgagttcc gtccaggcat cgaaaccact gagcgtaatt    2340
accgttacgc aggctggaaa aaagcggtta acgcgcgat ggcgtgggaa gaacacgacg    2400
aataa                                                                2405
```

<210> SEQ ID NO 20
<211> LENGTH: 2405
<212> TYPE: DNA
<213> ORGANISM: Artificial Sequence
<220> FEATURE:
<223> OTHER INFORMATION: Synthetic construct

<400> SEQUENCE: 20

```
atgagtcaaa catcaacctt gaaaggccag tgcattgctg aattcctcgg taccgggttg      60
ttgattttct tcggtgtggg ttgcgttgca gcactaaaag tcgctggtgc gtcttttggt     120 cagtggggaaa tcagtgtcat ttggggactg ggggtggcaa tggccatcta cctgaccgca    180
ggggtttccg cgcgcatct taatcccgct gttaccattg cattgtggct gtttgcctgt     240
ttcgacaagc gcaaagttat tccttttatc gtttcacaag ttgccggcgc tttctgtgct    300
gcggctttag tttacgggct ttactacaat ttattttcg acttcgagca gactcatcac    360
attgttcgcg gcagcgttga agtgttgat ctggctggca cttctctac ttaccctaat     420 cctcatatca attttgtgca ggctttcgca gttgagatgg tgattaccgc tattctgatg    480
gggctgatcc tggcgttaac ggacgatggc aacggtgtac cacgcggccc tttggctccc    540
ttgctgattg gtctactgat tgcggtcatt ggcgcatcta tgggcccatt gacaggttt     600 gccatgaacc cagcgcgtga cttcggtccg aaagtctttg cctggctggc gggctggggc    660
aatgtcgcct ttaccggcgg cagagacatt ccttacttcc tggtgccgct tttcggccct    720
atcgttggcg cgattgtagg tgcatttgcc taccgcaaac tgattggtcg ccatttgcct    780
tgcgatatct gtgttgtgga agaaaaggaa accacaactc cttcagaaca aaaagcttcg    840
ctgtaatatg actacgggac aattaaacat gactgaaaaaa aatatatcg ttgcgcatga    900 ctgaaaaaaa atatatcgtt gcgctcgacc agggcaccac cagctcccgc gcggtcgtaa    960
tggatcacga tgccaatatc attagcgtgt cgcagcgcga atttgagcaa atctacccaa   1020
aaccaggttg ggtagaacac gacccaatgg aaatctgggc cacccaaagc tccacgctgg   1080
tagaagtgct ggcgaaagcc gatatcagtt ccgatcaaat tgcagctatc ggtattacga   1140
accagcgtga accactatt gtctgggaaa agaaaccgg caagcctatc tataacgcca    1200
ttgtctggca gtgccgtcgt accgcagaaa tctgcgagca tttaaaacgt gacggtttag   1260
aagattatat ccgcagcaat accggtctgg tgattgaccc gtactttct ggcaccaaag    1320 tgaagtggat cctcgaccat gtggaaggct ctcgcgagcg tgcacgtcgt ggtgaattgc   1380
tgtttggtac ggttgatacg tggcttatct ggaaaatgac tcagggccgt gtccatgtga   1440
ccgattacac caacgcctct cgtaccagtg tgttcaacat ccatacctg gactgggacg    1500 acaaaatgct ggaagtgctg gatattccgc gcagagatgct gccagaagtg cgtcgttctt   1560
```

| | |
|---|---|
| ccgaagtata cggtcagact aacattggcg gcaaaggcgg cacgcgtatt ccaatctccg | 1620 |
| ggatcgccgg tgaccagcag gccgcgctgt ttggtcagtt gtgcgtgaaa gaagggatgg | 1680 |
| cgaagaacac ctatggcact ggctgcttta tgctgatgaa cactggcgag aaagcggtga | 1740 |
| aatcagaaaa cggcctgctg accaccatcg cctgcggccc gactggcgaa gtgaactatg | 1800 |
| cgttggaagg tgcggtgttt atggcaggcg catccattca gtggctgcgc gatgaaatga | 1860 |
| agttgattaa cgacgcctac gattccgaat atttcgccac caaagtgcaa acaccaatg | 1920 |
| gtgtgtatgt ggttccggca tttaccgggc tgggtgcgcc gtactgggac ccgtatgcgc | 1980 |
| gcggggcgat tttcggtctg actcgtgggg tgaacgctaa ccacattata cgcgcgacgc | 2040 |
| tggagtctat tgcttatcag acgcgtgacg tgctggaagc gatgcaggcc gactctggta | 2100 |
| tccgtctgca cgccctgcgc gtggatggtg gcgcagtagc aaacaatttc ctgatgcagt | 2160 |
| tccagtccga tattctcggc acccgcgttg agcgcccgga agtgcgcgaa gtcaccgcat | 2220 |
| tgggtgcggc ctatctcgca ggcctggcgg ttggcttctg gcagaacctc gacgagctgc | 2280 |
| aagagaaagc ggtgattgag cgcgagttcc gtccaggcat cgaaaccact gagcgtaatt | 2340 |
| accgttacgc aggctggaaa aaagcggtta acgcgcgat ggcgtgggaa gaacacgacg | 2400 |
| aataa | 2405 |

<210> SEQ ID NO 21
<211> LENGTH: 6538
<212> TYPE: DNA
<213> ORGANISM: Artificial Sequence
<220> FEATURE:
<223> OTHER INFORMATION: Synthetic construct

<400> SEQUENCE: 21

| | |
|---|---|
| gatctttggg agcagtcctt gtgcgcttac gaggtgagcc ggtggggaac cgttatctgc | 60 |
| ctatggtgtg agcccccta gagagcttca agagcaatca gcccgaccta gaaaggaggc | 120 |
| caagagagag acccctacgg ggggaaccgt tttctgccta cgagatggca catttactgg | 180 |
| gaagctttac ggcgtcctcg tggaagttca atgcccgcag acttaagtgc tctattcacg | 240 |
| gtctgacgtg acacgctaaa ttcagacata gcttcattga ttgtcgccac gagccagtct | 300 |
| ctccctcaac agtcataaac caacctgcaa tggtcaagcg atttccttta gctttcctag | 360 |
| cttgtcgttg actggactta gctagttttt ctcgctgtgc tcgggcgtac tcactgtttg | 420 |
| ggtctttcca gcgttctgcg gccttttttac cgccacgtct tcccatagtg ccagagctt | 480 |
| ttcgccctcg gctgctctgc gtctctgtct gacgagcagg gacgactggc tggccttag | 540 |
| cgacgtagcc gcgcacacgt cgcgccatcg tctggcggtc acgcatcggc ggcagatcag | 600 |
| gctcacggcc gtctgctccg accgcctgag cgacggtgta ggcacgctcg taggcgtcga | 660 |
| tgatcttggt gtcttttagg cgctcaccag ccgcttttaa ctggtatccc acagtcaaag | 720 |
| cgtggcgaaa agccgtctca tcacgggcgg cacgccctgg agcagtccag aggacacgga | 780 |
| cgccgtcgat cagctctcca gacgcttcag cggcgctcgg caggcttgct tcaagcgtgg | 840 |
| caagtgcttt tgcttccgca gtggcttttc ttgccgcttc gatacgtgcc cgtccgctag | 900 |
| aaaactcctg ctcatagcgt tttttaggtt tttctgtgcc tgagatcatg cgagcaacct | 960 |
| ccataagatc agctaggcga tccacgcgat tgtgctgggc atgccagcgg tacgcggtgg | 1020 |
| gatcgtcgga gacgtgcagt ggccaccggc tcagcctatg tgaaaagcc tggtcagcgc | 1080 |
| cgaaaacgcg ggtcatttcc tcggtcgttg cagccagcag gcgcatattc gggctgctca | 1140 |

```
tgcctgctgc ggcatacacc ggatcaatga gccagatgag ctggcatttc ccgctcagtg    1200
gattcacgcc gatccaagct ggcgcttttt ccaggcgtgc ccagcgctcc aaaatcgcgt    1260
agacctcggg gtttacgtgc tcgatttttc cgccggcctg gtggctcggc acatcaatgt    1320
ccaggacaag cacggctgcg tgctgcgcgt cgtcagagc aacatactgg caccgggcaa    1380
gcgattttga accaactcgg tataacttcg gctgtgtttc tcccgtgtcc gggtctttga    1440
tccaagcgct ggcgaagtcg cgggtcttgc tgccctggaa attttctctg cccaggtgag    1500
cgaggaattc gcggcggtct tcgctcgtcc agccacgtga tcgcagcgcg agctcgggat    1560
gggtgtcgaa cagatcagcg gaaaatttcc aggccggtgt gtcaatgtct cgtgaatccg    1620
ctagagtcat ttttgagcgc tttctcccag gtttggactg ggggttagcc gacgccctgt    1680
gagttaccgc tcacgggcg ttcaacattt ttcaggtatt cgtgcagctt atcgcttctt    1740
gccgcctgtg cgcttttttcg acgcgcgacg ctgctgccga ttcggtgcag gtggtggcgg    1800
cgctgacacg tcctgggcgg ccacggccac acgaaacgcg gcatttacga tgtttgtcat    1860
gcctgcgggc accgcgccac gatcgcggat aattctcgct gccgcttcca gctctgtgac    1920
gaccatggcc aaaatttcgc tcggggacg cacttccagc gccatttgcg acctagccgc    1980
ctccagctcc tcggcgtggc gtttgttggc gcgctcgcgg ctggctgcgg cacgacacgc    2040
atctgagcaa tattttgcgc gccgtcctcg cgggtcaggc cggggaggaa tcaggccacc    2100
gcagtaggcg caactgattc gatcctccac tactgtgcgt cctcctggcg ctgccgagca    2160
cgcagctcgt cagccagctc ctcaagatcc ggccacgagag tttctaggtc gctcgcggca    2220
ctggcccagt ctcgtgatgc tggcgcgtcc gtcgtatcga gagctcggaa aaatccgatc    2280 accgtttta aatcgacggc agcatcgagc gcgtcggact ccagcgcgac atcagagaga    2340
tccatagctg atgattcggg ccaattttgg tacttcgtcg tgaaggtcat gacaccatta    2400
taacgaacgt tcgttaaagt ttttggcgga aaatcacgcg gcacgaaaat tttcacgaag    2460
cgggactttg cgcagctcag gggtgctaaa aattttgtat cgcacttgat ttttccgaaa    2520
gacagattat ctgcaaacgg tgtgtcgtat ttctggcttg gttttttaaaa aatctggaat    2580 cgaaaatttg cgggcgacc gagaagttttt ttacaaaagg caaaaacttt ttcgggatcg    2640
acagaaataa aacgatcgac ggtacgcaac aaaaaagcgt caggatcgcc gtagagcgat    2700
tgaagaccgt caaccaaagg ggaagcctcc aatcgacgcg acgcgcgctc tacggcgatc    2760
ctgacgcaga ttttttagcta tctgtcgcag cgccctcagg gacaagccac ccgcacaacg    2820
tcgcgagggc gatcagcgac gccgcagtac tgatcctccg gcgttcagcc tgtgccacag    2880
ccgacaggat ggtgaccgcg caattaaccc tcactaaagg gaacaaaagc tgggtaccgg    2940
gccccccctc gaggtcgacg gtacctctat ctggtgccct aaacggggga atattaacgg    3000
gcccagggtg gtcgcaccctt ggttggtagg agtagcatgg gatcctctag aggcccagcc    3060
ggccattata attaggcctc ggggggccgcg ccgctgcct ggcggcagta gcgcggtggt    3120
cccacctgac cccatgccga actcagaagt gaaacgccgt agcgccgatg gtagtgtggg    3180
gtctccccat gcgagagtag ggaactgcca ggcatcaaat aaaacgaaag gctcagtcga    3240
aagactgggc ctttcgtttt atctgttgtt tgtcggtgaa cgctctcctg agtaggacaa    3300
atccgccggg agcggatttg aacgttgcga agcaacggcc cggagggtgg cgggcaggac    3360
gcccgccata aactgccagg catcaaatta agcagaaggc catcctgacg gatggccttt    3420
tgccaccgcg gtggagctcc aattcgccct atagtgagtc gtattacgcg cggtgaccac    3480
catttgcccc atatcaccgt cggtactgat cccgtcgtca ataaaccgaa ccgctacacc    3540
```

```
ctgagcatca aactctttta tcagttggat catgtcggcg gtgtcgcggc caagacggtc    3600
gagcttcttc accagaatga catcaccttc ctccaccttc atcctcagca aatccagccc    3660
ttcccgatct gttgaactgc cggatgcctt gtcggtaaag atgcggttag cttttacccc    3720
tgcatctttg agcgctgagg tctgcctcgt gaagaaggtg ttgctgactc ataccaggcc    3780
tgaatcgccc catcatccag ccagaaagtg agggagccac ggttgatgag agctttgttg    3840
taggtggacc agttggtgat tttgaacttt tgctttgcca cggaacggtc tgcgttgtcg    3900
ggaagatgcg tgatctgatc cttcaactca gcaaaagttc gatttattca acaaagccgc    3960
cgtcccgtca gtcagcgta atgctctgcc agtgttacaa ccattcaaat atgtatccgc    4020
tgagcaataa ctagcataac cccttggggc tctaaacgg gtcttgaggg gttttttgct    4080
gaaacctcag gcatttgaga agcacacggt cacactgctt ccggtagtca ataaaccggt    4140
aaaccagcaa tagacataag cggctatttta acgaccctgc cctgaaccga cgaccgggtc    4200
atcgtggccg gatcttgcgg cccctcggct gaacgaatt gttagacatt atttgccgac    4260
taccttggtg atctcgcctt tcacgtagtg gacaaattct tccaactgat ctgcgcgcga    4320
ggccaagcga tcttcttctt gtccaagata agcctgtcta gcttcaagta tgacgggctg    4380
atactgggcc ggcaggcgct ccattgccca gtcggcagcg acatccttcg gcgcgatttt    4440
gccggttact cgcgctgtacc aaatgcggga caacgtaagc actacatttc gctcatcgcc    4500
agcccagtcg ggcggcgagt tccatagcgt taaggtttca tttagcgcct caaatagatc    4560
ctgttcagga accggatcaa agagttcctc cgccgctgga cctaccaagg caacgctatg    4620
ttctcttgct tttgtcagca agatagccag atcaatgtcg atcgtggctg gctcgaagat    4680
acctgcaaga atgtcattgc gctgccattc tccaaattgc agttcgcgct tagctggata    4740
acgccacgga atgatgtcgt cgtgcacaac aatggtgact tctacagcgc ggagaatctc    4800
gctctctcca ggggaagccg aagtttccaa aaggtcgttg atcaaagctc gccgcgttgt    4860
ttcatcaagc cttacggtca ccgtaaccag caaatcaata tcactgtgtg gcttcaggcc    4920
gccatccact gcggagccgt acaaatgtac ggccagcaac gtcggttcga gatgcgctc    4980 gatgacgcca actacctctg atagttgagt cgatacttcg gcgatcaccg cttccctcat    5040
actcttcctt tttcaatatt attgaagcat ttatcagggt tattgtctca tgagcggata    5100
catatttgaa tgtatttaga aaataaaca aatagctagc tcactcggtc ggagtgtata    5160
ctggcttact atggctgagt tgaaggatca gatcacgcat cttcccgaca acgcagaccg    5220
ttccgtggca aagcaaaagt tcaaaatcac caactggtcc acctacaaca aagctctcat    5280
caaccgtggc tccctcactt tctggctgga tgatggggcg attcaggcct ggtatgagtc    5340
agcaacacct tcttcacgag gcagacctca gcgctagcgg agtgtatact ggcttactat    5400
gttggcactg atgagggtgt cagtgaagtg cttcatgtgg caggagaaaa aaggctgcac    5460
cggtgcgtca gcagaatatg tgatacagga tatattccgc ttcctcgctc actgactcgc    5520
tacgctcggt cgttcgactg cggcgagcgg aaatggctta cgaacggggc ggagatttcc    5580
tggaagatgc caggaagata cttaacaggg aagtgagagg gccgcggcaa agccgttttt    5640
ccataggctc cgcccccctg acaagcatca cgaaatctga cgctcaaatc agtggtggcg    5700
aaacccgaca ggactataaa gataccaggc gtttccccct ggcggctccc tcgtgcgctc    5760
tcctgttcct gcctttcggt ttaccggtgt cattccgctg ttatggccgc gtttgtctca    5820
ttccacgcct gacactcagt tccgggtagg cagttcgctc caagctggac tgtatgcacg    5880
```

| | |
|---|---|
| aaccccccgt tcagtccgac cgctgcgcct tatccggtaa ctatcgtctt gagtccaacc | 5940 |
| cggaaagaca tgcaaaagca ccactggcag cagccactgg taattgattt agaggagtta | 6000 |
| gtcttgaagt catgcgccgg ttaaggctaa actgaaagga caagttttgg tgactgcgct | 6060 |
| cctccaagcc agttacctcg gttcaaagag ttggtagctc agagaacctt cgaaaaaccg | 6120 |
| ccctgcaagg cggttttttc gttttcagag caagagatta cgcgcagacc aaaacgatct | 6180 |
| caagaagatc atcttattaa ggggtctgac gctcagtgga acgaaaactc acgttaaggg | 6240 |
| attttggtca tgagattatc aaaaaggatc ttcacctaga tccttttaaa ttaaaaatga | 6300 |
| agttttaaat caatctaaag tatatatgag taaacttggt ctgacagtta ccaatgctta | 6360 |
| atcagtgagg cacctatctc agcgatctgt ctatttcgtt catccatagt tgcctgactc | 6420 |
| cccgtcgtgt agataactac gatacgggag ggcttaccat ctggccccag tgctgcaatg | 6480 |
| ataccgcgag acccacgctc accggctcca gatttatcag caataaacca gccagccg | 6538 |

<210> SEQ ID NO 22
<211> LENGTH: 8084
<212> TYPE: DNA
<213> ORGANISM: Artificial Sequence
<220> FEATURE:
<223> OTHER INFORMATION: Synthetic construct

<400> SEQUENCE: 22

| | |
|---|---|
| ccaagcttgg ctgttttggc ggatgagaga agattttcag cctgatacag attaaatcag | 60 |
| aacgcagaag cggtctgata aaacagaatt tgcctggcgg cagtagcgcg gtggtcccac | 120 |
| ctgaccccat gccgaactca gaagtgaaac gccgtagcgc cgatggtagt gtggggtctc | 180 |
| cccatgcgag agtagggaac tgccaggcat caaataaaac gaaaggctca gtcgaaagac | 240 |
| tgggcctttc gttttatctg ttgtttgtcg gtgaacgctc tcctgagtag acaaatccg | 300 |
| ccgggagcgg atttgaacgt tgcgaagcaa cggcccggag ggtggcgggc aggacgcccg | 360 |
| ccataaactg ccaggcatca aattaagcag aaggccatcc tgacggatgg cctttttgcg | 420 |
| tttctacaaa ctcttttgtt tattttttcta aatacattca aatatgtatc cgctcatgag | 480 |
| acaataaccc tgataaatgc ttcaataata ttgaaaaagg aagagtatga gtattcaaca | 540 |
| tttccgtgtc gcccttattc ccttttttgc ggcattttgc cttcctgttt ttgctcaccc | 600 |
| agaaacgctg gtgaaagtaa aagatgctga agatcagttg ggtgcacgag tgggttacat | 660 |
| cgaactggat ctcaacagcg gtaagatcct tgagagtttt cgccccgaag aacgttttcc | 720 |
| aatgatgagc acttttaaag ttctgctatg tggcgcggta ttatcccgtg ttgacgccgg | 780 |
| gcaagagcaa ctcggtcgcc gcatacacta ttctcagaat gacttggttg agtaattcgt | 840 |
| aatcatgtca tagctgtttc ctgtgtgaaa ttgttatccg ctcacaattc cacacaacat | 900 |
| acgagccgga agcataaagt gtaaagcctg gggtgcctaa tgagtgagct aactcacatt | 960 |
| aattgcgttg cgctcactgc ccgctttcca gtcgggaaac ctgtcgtgcc agctgcatta | 1020 |
| atgaatcggc caacgcgcgg ggagaggcgg tttgcgtatt gggcgctctt ccgcttcctc | 1080 |
| gctcactgac tcgctgcgct cggtcgttcg gctgcggcga gcggtatcag ctcactcaaa | 1140 |
| ggcggtaata cggttatcca cagaatcagg ggataacgca ggaaagaaca tgtgagcaaa | 1200 |
| aggccagcaa aaggccagga accgtaaaaa ggccgcgttg ctggcgtttt tccataggct | 1260 |
| ccgcccccct gacgagcatc acaaaaatcg acgctcaagt cagaggtggc gaaacccgac | 1320 |
| aggactataa agataccagg cgtttccccc tggaagctcc ctcgtgcgct ctcctgttcc | 1380 |
| gaccctgccg cttaccggat acctgtccgc ctttctccct tcgggaagcg tggcgctttc | 1440 |

```
tcatagctca cgctgtaggt atctcagttc ggtgtaggtc gttcgctcca agctgggctg   1500
tgtgcacgaa ccccccgttc agcccgaccg ctgcgcctta tccggtaact atcgtcttga   1560
gtccaacccg gtaagacacg acttatcgcc actggcagca gccactggta acaggattag   1620
cagagcgagg tatgtaggcg gtgctacaga gttcttgaag tggtggccta actacggcta   1680
cactagaaga acagtatttg gtatctgcgc tctgctgaag ccagttacct tcggaaaaag   1740
agttggtagc tcttgatccg gcaaacaaac caccgctggt agcggtggtt ttttgtttg   1800 caagcagcag attacgcgca gaaaaaagg atcctttga tcttttctac   1860 ggggtctgac gctcagtgga acgaaaactc acgttaaggg attttggtca tgagattatc   1920
aaaaaggatc ttcacctaga tccttttggg ggggggggga aagccacgtt gtgtctcaaa   1980
atctctgatg ttacattgca caagataaaa atatatcatc atgaacaata aaactgtctg   2040
cttacataaa cagtaataca agggggtgtta tgagccatat tcaacgggaa acgtcttgct   2100
cgaggccgcg attaaattcc aacatggatg ctgatttata tgggtataaa tgggctcgcg   2160
ataatgtcgg gcaatcaggt gcgacaatct atcgattgta tgggaagccc gatgcgccag   2220
agttgtttct gaaacatggc aaaggtagcg ttgccaatga tgttacagat gagatggtca   2280
gactaaactg gctgacggaa tttatgcctc ttccgaccat caagcatttt atccgtactc   2340
ctgatgatgc atggttactc accactgcga tccccgggaa aacagcattc caggtattag   2400
aagaatatcc tgattcaggt gaaaatattg ttgatgcgct ggcagtgttc ctgcgccggt   2460
tgcattcgat tcctgtttgt aattgtcctt ttaacagcga tcgcgtattt cgtctcgctc   2520
aggcgcaatc acgaatgaat aacggtttgg ttgatgcgag tgattttgat gacgagcgta   2580
atggctggcc tgttgaacaa gtctggaaag aaatgcataa gcttttgcca ttctcaccgg   2640
attcagtcgt cactcatggt gatttctcac ttgataacct tattttttgac gagggggaaat   2700 taataggttg tattgatgtt ggacgagtcg gaatcgcaga ccgataccag gatcttgcca   2760
tcctatggaa ctgcctcggt gagttttctc cttcattaca gaaacggctt tttcaaaaat   2820
atggtattga taatcctgat atgaataaat tgcagtttca tttgatgctc gatgagtttt   2880
tctaatcaga attggttaat tggttgtaac actggcagag cattacgctg acttgacggg   2940
acggcggctt tgttgaataa atcgaacttt gctgagttg aaggatcaga tcacgcatct   3000
tcccgacaac gcagaccgtt ccgtggcaaa gcaaaagttc aaaatcacca actggtccac   3060
ctacaacaaa gctctcatca accgtggctc cctcactttc tggctggatg atggggcgat   3120
tcaggcctgg tatgagtcag caacaccttc ttcacgaggc agacctcagc gccccccccc   3180
ccctagcttg tctacgtctg atgctttgaa tcggacggac ttgccgatct tgtatgcggt   3240
gatttttccc tcgtttgccc acttttttaat ggtggccggg gtgagagcta cgcgggcggc   3300
gacctgctgc gctgtgatcc aatattcggg gtcgttcact ggttccccctt tctgatttct   3360 ggcatagaag aaccccgtg aactgtgtgg ttccggggt tgctgatttt tgcgagactt   3420
ctcgcgcaat tccctagctt aggtgaaaac accatgaaac actagggaaa cacccatgaa   3480
acacccatta gggcagtagg gcggcttctt cgtctagggc ttgcatttgg gcggtgatct   3540
ggtctttagc gtgtgaaagt gtgtcgtagg tggcgtgctc aatgcactcg aacgtcacgt   3600
catttaccgg gtcacggtgg gcaaagagaa ctagtgggtt agacattgtt ttcctcgttg   3660
tcggtggtgg tgagcttttc tagccgctcg gtaaacgcgg cgatcatgaa ctcttggagg   3720
ttttcaccgt tctgcatgcc tgcgcgcttc atgtcctcac gtagtgccaa aggaacgcgt   3780
```

```
gcggtgacca cgacgggctt agcctttgcc tgcgcttcta gtgcttcgat ggtggcttgt    3840
gcctgcgctt gctgcgcctg tagtgcctgt tgagcttctt gtagttgctg ttctagctgt    3900
gccttggttg ccatgcttta agactctagt agctttcctg cgatatgtca tgcgcatgcg    3960
tagcaaacat tgtcctgcaa ctcattcatt atgtgcagtg ctcctgttac tagtcgtaca    4020
tactcatatt tacctagtct gcatgcagtg catgcacatg cagtcatgtc gtgctaatgt    4080
gtaaaacatg tacatgcaga ttgctggggg tgcaggggc ggagccaccc tgtccatgcg     4140
gggtgtgggg cttgccccgc cggtacagac agtgagcacc ggggcaccta gtcgcggata    4200
ccccccctag gtatcggaca cgtaaccctc ccatgtcgat gcaaatcttt aacattgagt    4260
acgggtaagc tggcacgcat agccaagcta ggcggccacc aaacaccact aaaaattaat    4320
agttcctaga caagacaaac cccgtgcga gctaccaact catatgcacg ggggccacat     4380
aacccgaagg ggtttcaatt gacaaccata gcactagcta agacaacggg cacaacaccc    4440
gcacaaactc gcactgcgca accccgcaca acatcgggtc taggtaacac tgaaatagaa    4500
gtgaacacct ctaaggaacc gcaggtcaat gagggttcta aggtcactcg cgctagggcg    4560
tggcgtaggc aaaacgtcat gtacaagatc accaatagta aggctctggc ggggtgccat    4620
aggtggcgca gggacgaagc tgttgcggtg tcctggtcgt ctaacggtgc ttcgcagttt    4680
gagggtctgc aaaactctca ctctcgctgg gggtcacctc tggctgaatt ggaagtcatg    4740
ggcgaacgcc gcattgagct ggctattgct actaagaatc acttggcggc gggtggcgcg    4800
ctcatgatgt ttgtgggcac tgttcgacac aaccgctcac agtcatttgc gcaggttgaa    4860
gcgggtatta agactgcgta ctcttcgatg gtgaaaacat ctcagtggaa gaagaacgt     4920
gcacggtacg gggtggagca cacctatagt gactatgagg tcacagactc ttgggcgaac    4980
ggttggcact gcaccgcaa catgctgttg ttcttggatc gtccactgtc tgacgatgaa     5040
ctcaaggcgt ttgaggattc catgttttcc cgctggtctg ctggtgtggt taaggccggt    5100
atggacgcgc cactgcgtga gcacgggtc aaacttgatc aggtgtctac ctggggtgga     5160
gacgctgcga aaatggcaac ctacctcgct aagggcatgt ctcaggaact gactggctcc    5220
gctactaaaa ccgcgtctaa ggggtcgtac acgccgtttc agatgttgga tatgttggcc    5280
gatcaaagcg acgccggcga ggatatggac gctgttttgg tggctcggtg gcgtgagtat    5340
gaggttggtt ctaaaaacct gcgttcgtcc tggtcacgtg gggctaagcg tgctttgggc    5400
attgattaca tagacgctga tgtacgtcgt gaaatggaag aagaactgta caagctcgcc    5460
ggtctggaag caccggaacg ggtcgaatca acccgcgttg ctgttgcttt ggtgaagccc    5520
gatgattgga aactgattca gtctgatttc gcggttaggc agtacgttct agattgcgtg    5580
gataaggcta aggacgtggc cgctgcgcaa cgtgtcgcta atgaggtgct ggcaagtctg    5640
ggtgtggatt ccaccccgtg catgatcgtt atggatgatg tggacttgga cgcggttctg    5700
cctactcatg gggacgctac taagcgtgat ctgaatgcgg cggtgttcgc gggtaatgag    5760
cagactattc ttcgcaccca ctaaaagcgg cataaacccc gttcgatatt ttgtgcgatg    5820
aatttatggt caatgtcgcg ggggcaaact atgatgggtc ttgttgttga caatggctga    5880
tttcatcagg aatggaactg tcatgctgtt atgtgcctgg ctcctaatca aagctgggga    5940
caatggggttg ccccgttgat ctgatctagt tcggattggc ggggcttcac tgtatctggg    6000
ggtggcatcg tgaatagatt gcacaccgta gtgggcagtg tgcacaccat agtggccatg    6060
agcaccacca cccccaggga cgccgacggc gcgaagctct cgcctggtg cggctcgag      6120
atcaagcaat ccggcgtcgg ccggagccgg gactactgcc gccgctcctg ccgccagcgg    6180
```

```
gcgtacgagg cccggcgcca gcgcgaggcg atcgtgtccg ccgtggcgtc ggcagtcgct    6240
cgccgagata cgtcacgtga cgaaatgcag cagccttcca ttccgtcacg tgacgaaact    6300
cgggccgcag gtcagagcac ggttccgccc gctccggccc tgccggaccc ccggcatccc    6360
gcaagaggcc cggcagtacc ggcataacca agcctatgcc tacagcatcc agggtgacgg    6420
tgccgaggat gacgatgagc gcattgttag atttcataca cggtgcctga ctgcgttagc    6480
aatttaactg tgataaacta ccgcattaaa gcttatcgat gataagctgt caaacatggc    6540
ctgtcgcttg cggtattcgg aatcttgcac gccctcgctc aagccttcgt cactggtccc    6600
gccaccaaac gtttcggcga agcaggcc attatcgccg gcatggcggc cgacgcgcgg    6660
ggagaggcgg tttgcgtatt gggcgccagg gtggtttttc ttttcaccag tgagacgggc    6720
aacagctgat tgcccttcac cgcctggccc tgagagagtt gcagcaagcg gtccacgctg    6780
gtttgcccca gcaggcgaaa atcctgtttg atggtggtta acggcgggat ataacatgag    6840
ctgtcttcgg tatcgtcgta tcccactacc gagatatccg caccaacgcg cagcccggac    6900
tcggtaatgg cgcgcattgc gcccagcgcc atctgatcgt tggcaaccag catcgcagtg    6960
ggaacgatgc cctcattcag catttgcatg gtttgttgaa aaccggacat ggcactccag    7020
tcgccttccc gttccgctat cggctgaatt tgattgcgag tgagatattt atgccagcca    7080
gccagacgca gacgcgccga gacagaactt aatgggcccg ctaacagcgc gatttgctgg    7140
tgacccaatg cgaccagatg ctccacgccc agtcgcgtac cgtcttcatg ggagaaaata    7200
atactgttga tgggtgtctg gtcagagaca tcaagaaata acgccggaac attagtgcag    7260
gcagcttcca cagcaatggc atcctggtca tccagcggat agttaatgat cagcccactg    7320
acgcgttgcg cgagaagatt gtgcaccgcc gctttacagg cttcgacgcc gcttcgttct    7380
accatcgaca ccaccacgct ggcacccagt tgatcggcgc gagatttaat cgccgcgaca    7440
atttgcgacg gcgcgtgcag ggccagactg gaggtggcaa cgccaatcag caacgactgt    7500
ttgcccgcca gttgttgtgc cacgcggttg ggaatgtaat tcagctccgc catcgccgct    7560 tccactttt cccgcgtttt cgcagaaacg tggctggcct ggttcaccac gcgggaaacg    7620
gtctgataag agacaccggc atactctgcg acatcgtata acgttactgg tttcacattc    7680
accaccctga attgactctc ttccgggcgc tatcatgcca taccgcgaaa ggttttgcac    7740
cattcgatgg tgtcaacgta aatgcatgcc gcttcgcctt cgcgcgcgaa ttgcaagctg    7800
atccgggctt atcgactgca cggtgcacca atgcttctgg cgtcaggcag ccatcggaag    7860
ctgtggtatg gctgtgcagg tcgtaaatca ctgcataatt cgtgtcgctc aaggcgcact    7920
cccgttctgg ataatgtttt tgcgccgac atcataacgg ttctggcaaa tattctgaaa    7980
tgagctgttg acaattaatc atcggctcgt ataatgtgtg gaattgtgag cggataacaa    8040
tttcacacag gaaacagaat tcccggggat ccgtcgacct gcag                    8084
```

<210> SEQ ID NO 23
<211> LENGTH: 5095
<212> TYPE: DNA
<213> ORGANISM: Artificial Sequence
<220> FEATURE:
<223> OTHER INFORMATION: Synthetic construct

<400> SEQUENCE: 23

```
gaattcacag gaaacagacc atgaacaact ttaatctgca cacccccaacc cgcattctgt     60 ttggtaaagg cgcaatcgct ggtttacgcg aacaaattcc tcacgatgct cgcgtattga    120
```

```
ttacctacgg cggcggcagc gtgaaaaaaa ccggcgttct cgatcaagtt ctggatgccc    180
tgaaaggcat ggacgtgctg gaatttggcg gtattgagcc aaacccggct tatgaaacgc    240
tgatgaacgc cgtgaaactg gttcgcgaac agaaagtgac tttcctgctg gcggttggcg    300
gcggttctgt actggacggc accaaattta tcgccgcagc ggctaactat ccggaaaata    360
tcgatccgtg gcacattctg caaacgggcg gtaaagagat taaaagcgcc atcccgatgg    420
gctgtgtgct gacgctgcca gcaaccggtt cagaatccaa cgcaggcgcg gtgatctccc    480
gtaaaaccac aggcgacaag caggcgttcc attctgccca tgttcagccg gtatttgccg    540
tgctcgatcc ggtttatacc tacaccctgc cgccgcgtca ggtggctaac ggcgtagtgg    600
acgcctttgt acacaccgtg aacagtatg ttaccaaacc ggttgatgcc aaaattcagg    660
accgtttcgc agaaggcatt ttgctgacgc taatcgaaga tggtccgaaa gccctgaaag    720
agccagaaaa ctacgatgtg cgcgccaacg tcatgtgggc ggcgactcag gcgctgaacg    780
gtttgattgg cgctggcgta ccgcaggact gggcaacgca tatgctgggc cacgaactga    840
ctgcgatgca cggtctggat cacgcgcaaa cactggctat cgtcctgcct gcactgtgga    900
atgaaaaacg cgataccaag cgcgctaagc tgctgcaata tgctgaacgc gtctggaaca    960
tcactgaagg ttccgatgat gagcgtattg acgccgcgat tgccgcaacc cgcaatttct   1020
ttgagcaatt aggcgtgccg acccacctct ccgactacgg tctggacggc agctccatcc   1080
cggctttgct gaaaaaactg gaagagcacg gcatgaccca actgggcgaa atcatgaca    1140
ttacgttgga tgtcagccgc cgtatatacg aagccgcccg ctaaggatcc tctagagtcg   1200
acctgcaggc atgcaagctt ggctgttttg gcggatgaga agatttttc agcctgatac   1260
agattaaatc agaacgcaga agcggtctga taaaacagaa tttgcctggc ggcagtagcg   1320
cggtggtccc acctgacccc atgccgaact cagaagtgaa acgccgtagc gccgatggta   1380
gtgtggggtc tccccatgcg agagtaggga actgccaggc atcaaataaa acgaaaggct   1440
cagtcgaaag actgggcctt tcgttttatc tgttgtttgt cggtgaacgc tctcctgagt   1500
aggacaaatc cgccgggagc ggatttgaac gttgcgaagc aacggcccgg agggtggcgg   1560
gcaggacgcc cgccataaac tgccaggcat caaattaagc agaaggccat cctgacggat   1620
ggccttttg cgtttctaca actcttttt gtttatttt ctaaatacat tcaaatatgt   1680
atccgctcat gagacaataa ccctgataaa tgcttcaata atattgaaaa aggaagagta   1740
tgagtattca acatttccgt gtcgccctta ttcccttttt tgcggcattt tgccttcctg   1800
ttttgctca cccagaaacg ctggtgaaag taaaagatgc tgaagatcag ttgggtgcac   1860
gagtgggtta tcgaactg atctcaaca gcggtaagat ccttgagagt tttcgccccg   1920
aagaacgttt tccaatgatg agcacttta aagttctgct atgtggcgcg gtattatccc   1980
gtgttgacgc cgggcaagag caactcggtc gccgcataca ctattctcag aatgacttgg   2040
ttgagtaatt cactgccgt cgttttacaa cgtcgtgact gggaaaaccc tggcgttacc   2100
caacttaatc gccttgcagc acatcccct ttcgccagct ggcgtaatag cgaagaggcc   2160
cgcaccgatc gcccttccca acagttgcgg ggggggggg aaagccacgt tgtgtctcaa   2220
aatctctgat gttacattgc acaagataaa aatatatcat catgaacaat aaaactgtct   2280
gcttacataa acagtaatac aagggggtgtt atgagccata ttcaacggga aacgtcttgc   2340
tcgaggccgc gattaaattc caacatggat gctgatttat atgggtataa atgggctcgc   2400
gataatgtcg gcaatcagg tgcgacaatc tatcgattgt atgggaagcc cgatgcgcca   2460
gagttgtttc tgaaacatgg caaaggtagc gttgccaatg atgttacaga tgagatggtc   2520
```

```
agactaaaact ggctgacgga atttatgcct cttccgacca tcaagcattt tatccgtact   2580
cctgatgatg catggttact caccactgcg atccccggga aaacagcatt ccaggtatta   2640
gaagaatatc ctgattcagg tgaaaatatt gttgatgcgc tggcagtgtt cctgcgccgg   2700
ttgcattcga ttcctgtttg taattgtcct tttaacagcg atcgcgtatt tcgtctcgct   2760
caggcgcaat cacgaatgaa taacggtttg gttgatgcga gtgattttga tgacgagcgt   2820
aatggctggc ctgttgaaca agtctggaaa gaaatgcata agcttttgcc attctcaccg   2880
gattcagtcg tcactcatgg tgatttctca cttgataacc ttattttga cgaggggaaa   2940
ttaataggtt gtattgatgt tggacgagtc ggaatcgcag accgatacca ggatcttgcc   3000
atcctatgga actgcctcgg tgagttttct ccttcattac agaaacggct ttttcaaaaa   3060
tatggtattg ataatcctga tatgaataaa ttgcagtttc atttgatgct cgatgagttt   3120
ttctaatcag aattggttaa ttggttgtaa cactggcaga gcattacgct gacttgacgg   3180
gacggcggct tgttgaata aatcgaactt ttgctgagtt gaaggatcag atcacgcatc   3240
ttcccgacaa cgcagaccgt tccgtggcaa agcaaaagtt caaaatcacc aactggtcca   3300
cctacaacaa agctctcatc aaccgtggct ccctcacttt ctggctggat gatggggcga   3360
tcaggcctg gtatgagtca gcaacacctt cttcacgagg cagacctcag cgccccccc   3420
ccccgcaaac tattaactgg cgaactactt actctagctt cccggcaaca attaatagac   3480
tggatggagg cggataaagt tgcaggacca cttctgcgct cggcccttcc ggctggctgg   3540
tttattgctg ataaatctgg agccggtgag cgtgggtctc gcggtatcat tgcagcactg   3600
gggccagatg gtaagccctc ccgtatcgta gttatctaca cgacggggag tcaggcaact   3660
atggatgaac gaaatagaca gatcgctgag ataggtgcct cactgattaa gcattggtaa   3720
ctgtcagacc aagtttactc atatatactt tagattgatt taaaacttca ttttaattt   3780
aaaaggatct aggtgaagat cctttttgat aatctcatga ccaaaatccc ttaacgtgag   3840
ttttcgttcc actgagcgtc agaccccta ataagatgat cttcttgaga tcgttttggt   3900
ctgcgcgtaa tctcttgctc tgaaaacgaa aaaaccgcct tgcagggcgg ttttttcgaag   3960
gttctctgag ctaccaactc tttgaaccga ggtaactggc ttggaggagc gcagtcacca   4020
aaacttgtcc tttcagttta gccttaaccg gcgcatgact tcaagactaa ctcctctaaa   4080
tcaattacca gtggctgctg ccagtggtgc ttttgcatgt ctttccgggt tggactcaag   4140
acgatagtta ccggataagg cgcagcggtc ggactgaacg ggggggttcgt gcatacagtc   4200
cagcttggag cgaactgcct acccggaact gagtgtcagg cgtggaatga gacaaacgcg   4260
gccataacag cggaatgaca ccggtaaacc gaaaggcagg aacaggagag cgcacgaggg   4320
agccgccagg gggaaacgcc tggtatcttt atagtcctgt cgggtttcgc caccactgat   4380
ttgagcgtca gatttcgtga tgcttgtcag ggggcggag cctatggaaa aacggctttg   4440
ccgcggccct ctcacttccc tgttaagtat cttcctggca tcttccagga aatctccgcc   4500
ccgttcgtaa gccatttccg ctcgccgcag tcgaacgacc gagcgtagcg agtcagtgag   4560
cgaggaagcg gaatatatcc tgtatcacat attctgctga cgcaccggtg cagccttttt   4620
tctcctgcca catgaagcac ttcactgaca ccctcatcag tgccaacata gtaagccagt   4680
atacactccg ctagcaagga gatggcgccc aacagtcccc cggccacggg gcctgccacc   4740
atacccacgc cgaaacaagc gctcatgagc ccgaagtggc gagcccgatc ttccccatcg   4800
gtgatgtcgg cgatataggc gccagcaacc gcacctgtgg cgccggtgat gccggccacg   4860
```

```
atgcgtccgg cgtagaggat ccggagctta tcgactgcac ggtgcaccaa tgcttctggc    4920
gtcaggcagc catcggaagc tgtggtatgg ctgtgcaggt cgtaaatcac tgcataattc    4980
gtgtcgctca aggcgcactc ccgttctgga taatgttttt tgcgccgaca tcataacggt    5040
tctggcaaat attctgaaat gagctgttga caattaatca tcggctcgta taatg         5095
```

MUTANT MICROORGANISM HAVING ABILITY TO PRODUCE 1,3-PROPANEDIOL, AND METHOD FOR PREPARING 1,3-PDO BY USING SAME

CROSS-REFERENCE TO RELATED APPLICATIONS

This is a U.S. national phase under the provisions of 35 U.S.C. § 371 of International Patent Application No. PCT/KR19/00571 filed Jan. 15, 2019, which in turn claims priority of Korean Patent Application No. 10-2018-0005451 filed Jan. 16, 2018. The disclosures of such international patent application and Korean priority patent application are hereby incorporated herein by reference in their respective entireties, for all purposes.

REFERENCE TO SEQUENCE LISTING SUBMITTED VIA EFS-WEB

This application includes an electronically submitted sequence listing in .txt format. The .txt file contains an updated sequence listing entitled "525_SeqListing_ST25.txt" created on Jul. 23, 2020 and is 36,556 bytes in size. The sequence listing contained in this .txt file is part of the specification and is hereby incorporated by reference herein in its entirety.

DEPOSITED MICROORGANISM

In conformity with the requirements of 37 CFR § 1.801-1.809, a deposit of the biological material (mutant *Corynebacterium glutamicum* microorganism) identified herein as MBEL-HCC-C-13PDO1 was made by the applicants hereof on Feb. 1, 2023 at Korean Collection for Type Cultures (KCTC), Korea Research Institute of Bioscience and Biotechnology (KRIBB), 181, Ipsin-gil, Jeongeup-si, Jeollabuk-do 56212, Republic of Korea, for which a KCTC Deposit Receipt was issued on Feb. 17, 2023 (Accession Number: KCTC 15328BP), under and subject to the Budapest Treaty on the International Recognition of the Deposit of Microorganisms for the Purpose of Patent Procedure.

TECHNICAL FIELD

The present disclosure relates to a mutant microorganism having the ability to produce 1,3-propanediol (1,3-PDO) from glycerol and a method of producing 1,3-PDO using the same, and more particularly to a mutant microorganism in which a glycerol catabolic pathway and a 1,3-PDO biosynthetic pathway are introduced into a microorganism incapable of using glycerol as a carbon source, and a method of producing 1,3-PDO using the same.

BACKGROUND ART 1,3-propanediol (1,3-PDO) is a compound that is used as a monomer for synthesis of polymers such as polyether, polyurethane, and polytrimethylene terephthalate (PTT). As conventional production methods for 1,3-PDO, chemical synthesis methods are mainly used, including hydration of acrolein, hydroformylation of ethylene oxide in the presence of phosphine, or enzymatic conversion of glycerol. These chemical production methods have limitations because they include expensive and environmentally harmful production processes (Lee et al., *Renewable and Sustainable Energy Reviews*, 42(Supplement C): 963-972; U.S. Pat. No. 8,236,994 B2).

As biological methods, methods of producing 1,3-PDO using microorganisms are mainly performed using microorganisms such as *Klebsiella, Clostridia, Enterobacter, Citrobacter*, or *Lactobacilli*. These methods all convert glycerol directly into 1,3-PDO through two consecutive metabolic pathways by which glycerol is converted into 3-hydroxy-proprionaldehyde (3-HPA) by glycerol dehydratase and then 3-HPA is reduced into 1,3-PDO by 1,3-PDO oxidoreductase (FIG. 1). DuPont has already successfully commercialized 1,3-PDO by introducing the metabolic pathways into *E. coli*. However, most microorganisms that biosynthesize 1,3-PDO, including *E. coli*, have a disadvantage in that various kinds of byproducts such as formate, acetate, lactate, ethanol, and 2,3-butanediol are also produced.

*Corynebacterium glutamicum*, a Gram-positive facultative anaerobic bacterium, is widely used in fermentation processes for amino acid production. In addition, in order to produce various kinds of chemicals and fuels using *Corynebacterium glutamicum*, many metabolic engineering studies have been conducted with the goal of enabling *Corynebacterium glutamicum* to use various kinds of carbon sources. However, few studies have been conducted on the production of 1,3-PDO using *Corynebacterium glutamicum*. In addition, one study reported that *Corynebacterium glutamicum* uses glucose and glycerol as carbon sources, that cell growth thereof is promoted using glucose, and that *Corynebacterium glutamicum* produces glutamic acid together with 1,3-PDO from glycerol (Huang et al., *Scientific Reports*, 7: 42246, 2017).

Accordingly, the present inventors have made efforts to more efficiently produce 1,3-PDO using glycerol as a single carbon source, and as a result, have found that, when a mutant microorganism, obtained by introducing a glycerol facilitator-encoding gene, a glycerol kinase-encoding gene and a glycerol-3-phosphate dehydrogenase-encoding gene into a microorganism incapable of using glycerol as a single carbon source in order to construct a glycerol catabolic pathway and further introducing a glycerol reactivase-encoding gene and a 1,3-propanediol oxidoreductase-encoding gene in order to biosynthesize 1,3-PDO, is cultured in a medium containing glycerol as a single carbon source, it produces 1,3-PDO, thereby completing the present disclosure.

SUMMARY OF THE INVENTION

An object of the present disclosure is to provide a mutant microorganism in which a glycerol catabolic pathway is introduced and which is capable of growing using glycerol as a single carbon source.

Another object of the present disclosure is to provide a mutant microorganism in which a 1,3-POD biosynthesis pathway is introduced and which is capable of producing 1,3-PDO using glycerol as a single carbon source.

Still another object of the present disclosure is to provide a method of producing 1,3-PDO using a mutant microorganism that uses glycerol alone as a single carbon source.

To achieve the above objects, the present disclosure provides a mutant microorganism in which a glycerol facilitator-encoding gene, a glycerol kinase-encoding gene and a glycerol-3-phosphate dehydrogenase-encoding gene are introduced into a microorganism incapable of using glycerol as a single carbon source and which is capable of growing on glycerol as a single carbon source.

The present disclosure also provides a mutant microorganism in which a glycerol facilitator-encoding gene, a glycerol kinase-encoding gene, a glycerol-3-phosphate dehydrogenase-encoding gene, a glycerol dehydratase-encoding gene, a glycerol reactivase-encoding gene and a 1,3-propanediol oxidoreductase-encoding gene are introduced into a microorganism incapable of using glycerol as a single carbon source and which has the ability to produce 1,3-propanediol from glycerol.

The present disclosure also provides a method of producing 1,3-propanediol from glycerol, the method comprising steps of: (a) culturing, in a glycerol-containing medium, a mutant microorganism having the ability to produce 1,3-propanediol from glycerol, thereby producing 1,3-propanediol; and (b) collecting the produced 1,3-propanediol.

DETAILED DESCRIPTION AND PREFERRED EMBODIMENTS OF THE INVENTION

Figure 1:
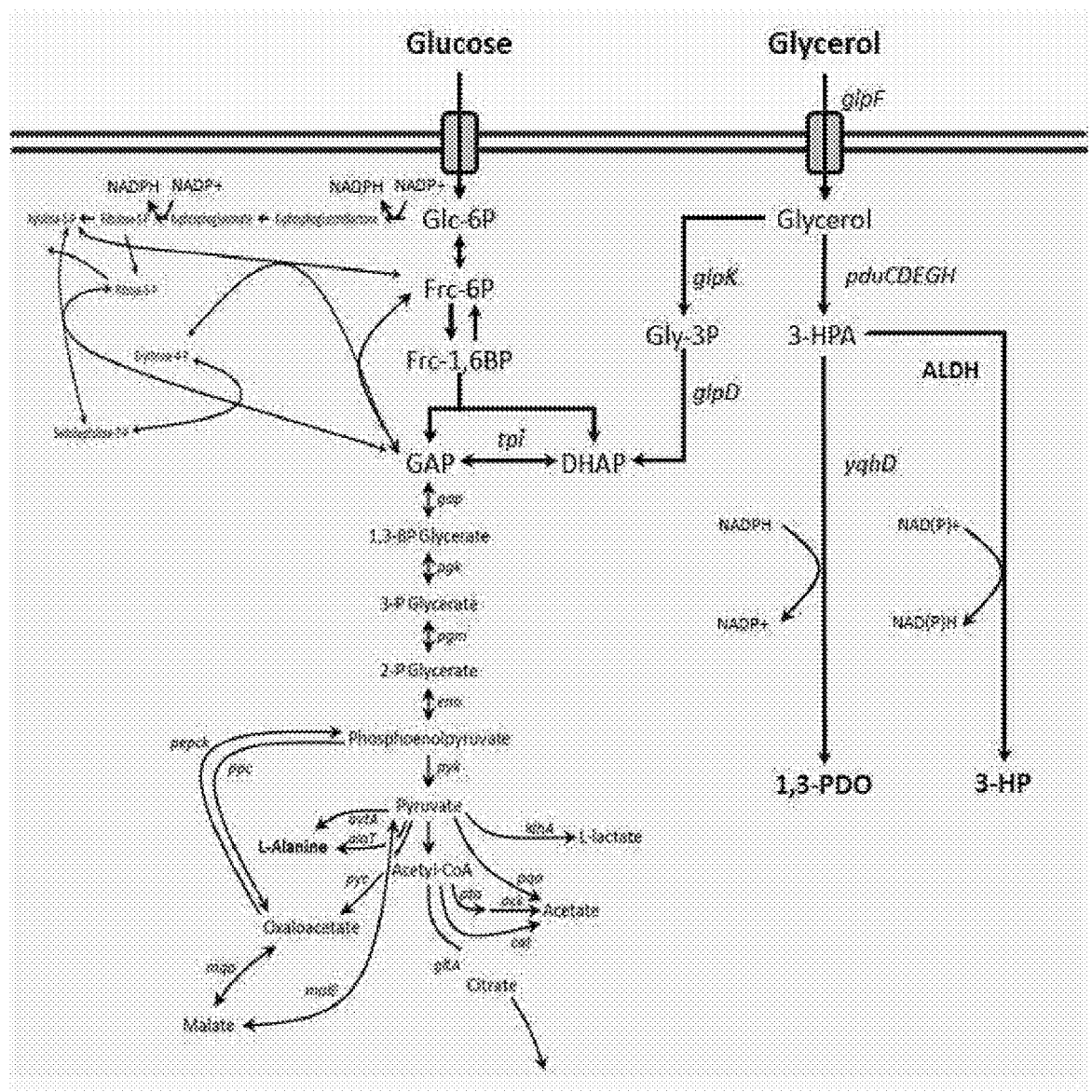
FIG. 1 is a schematic view of an overall metabolic pathway including a 1,3-PDO biosynthesis pathway and a glycerol catabolic pathway in Corynebacterium glutamicum.

Unless otherwise defined, all technical and scientific terms used in the present specification have the same meanings as commonly understood by those skilled in the art to which the present disclosure pertains. In general, the nomenclature used in the present specification is well known and commonly used in the art.

According to the present disclosure, a mutant microorganism was constructed, the cells of which are capable of cell growth through a constructed glycerol catabolic pathway using glycerol as a single carbon source and which produces 1,3-PDO through a constructed 1,3-PDO biosynthesis metabolic pathway. In the present disclosure, a mutant microorganism was constructed by introducing a glycerol facilitator-encoding gene, a glycerol kinase-encoding gene and a glycerol-3-phosphate dehydrogenase-encoding gene, which are responsible for the glycerol catabolic pathway, into a microorganism incapable of naturally using glycerol as a single carbon source, and it has been found that the mutant microorganism grows in a medium containing glycerol as a single carbon source.

Therefore, in one aspect, the present disclosure is directed to a mutant microorganism in which a glycerol facilitator-encoding gene, a glycerol kinase-encoding gene and a glycerol-3-phosphate dehydrogenase-encoding gene are introduced into a microorganism incapable of using glycerol as a single carbon source and which is capable of growing using glycerol as a single carbon source.

In the present disclosure, the glycerol facilitator-encoding gene, the glycerol kinase-encoding gene and the glycerol-3-phosphate dehydrogenase-encoding gene may be E. coli W3110-derived glpF, glpK and glpD, respectively.

In the present disclosure, the microorganism incapable of using glycerol as a single carbon source may be a microorganism such as *Corynebacterium* spp., *Lactobacillus panis*, *Clostridium acetobutylicum*, *Clostridium beijerinckii*, *Mycobacterium tuberculosis*, or *Rhodobacter capsulatus*, but is not limited thereto.

In the present disclosure, the genes may be overexpressed by strong promoters such as tac, trc, H36 or tuf.

In an embodiment of the present disclosure, glycerol kinase and glycerol-3-phosphate dehydrogenase were introduced into the microorganism *Corynebacterium glutamicum*, which is capable of diffusing glycerol naturally but is incapable of cell growth when glycerol is used as a single carbon source, and a glycerol facilitator was introduced into the microorganism to increase the glycerol uptake rate. As used herein, the term "introduction" refers to performing transformation by inserting the above-described enzymes into the *Corynebacterium glutamicum* genome or introducing a vector expressing the enzymes into the genome.

In an embodiment of the present disclosure, adaptive laboratory evolution (ALE) was performed to increase the uptake rate of glycerol in a microorganism in which the glycerol catabolic pathway is introduced or in a microorganism whose cell growth is significantly inhibited or low when glycerol is used. ALE refers to continuous transfer and culture of cells in a fresh medium. The time point at which cells are transferred is when cell growth in a pre-culture medium is observed and the pre-culture is inoculated into the next culture medium. The end point is when cells show enhanced cell growth during culture with a single carbon source at a desired glycerol concentration.

The present disclosure provides a method of shortening the lag phase of a mutant microorganism in a medium containing glycerol as a single carbon source, the method comprising steps of: (a) culturing a mutant microorganism, which is capable of growing on glycerol as a single carbon source, in a medium containing glycerol as a single carbon source; (b) inoculating a portion of the culture containing the mutant microorganism growth in step (a) into a fresh medium containing glycerol as a single carbon source; and (c) repeating steps (a) and (b) several times and collecting a microorganism with a reduced lag phase.

In an embodiment of the present disclosure, a mutant microorganism having enhanced ability to produce 1,3-PDO was produced by introducing, into the microorganism *Corynebacterium glutamicum*, which is incapable of naturally using glycerol as a single carbon source, a glycerol facilitator-encoding gene, a glycerol kinase-encoding gene and a glycerol-3-phosphate dehydrogenase-encoding gene, which are genes responsible for the glycerol catabolic pathway, so that the cells of the microorganism having the ability to produce 1,3-PDO are capable of growing using glycerol, and introducing a glycerol dehydratase-encoding gene, a glycerol reactivase-encoding gene and a 1,3-propanediol oxidoreductase-encoding gene, which are genes encoding the enzymes responsible for biosynthesis of 1,3-PDO, so that the microorganism has enhanced activity compared to the endogenous activity thereof. It was confirmed that the constructed mutant microorganism produced 1,3-PDO simultaneously with cell growth under a condition in which glycerol was used as a single carbon source.

In the present disclosure, the glycerol facilitator-encoding gene, the glycerol kinase-encoding gene and the glycerol-3-phosphate dehydrogenase-encoding gene may be glpF, glpK and glpD, respectively.

In the present disclosure, the glycerol facilitator-encoding gene, the glycerol kinase-encoding gene and the glycerol dehydrogenase-encoding gene may be glpF, glpK and glpD, respectively.

In the present disclosure, the glycerol dehydratase-encoding gene, the glycerol reactivase-encoding gene and the 1,3-propanediol oxidoreductase-encoding gene may be pduCDEG and yqhD, respectively.

In the present disclosure, the microorganism incapable of using glycerol as a single carbon source may be a microorganism such as *Corynebacterium* spp., *Lactobacillus panis*, *Clostridium acetobutylicum*, *Clostridium beijerinckii*, *Mycobacterium tuberculosis*, or *Rhodobacter capsulatus*, but is not limited thereto.

In the present disclosure, the genes may be overexpressed by a strong promoter selected from the group consisting of tac, trc, H36 and tuf.

In an embodiment of the present disclosure, as the glycerol dehydratase-encoding gene, the glycerol reactivase-encoding gene and the 1,3-propanediol oxidoreductase-encoding gene, which are introduced to impart or enhance the ability to produce 1,3-PDO, those derived from *Klebsiella pneumoniae* DSMZ2026 were used. In this case, the glycerol dehydratase-encoding gene and the glycerol reactivase-encoding gene may be dhaB1234gdrAB or pduCDEGH, which is a gene cluster fragment, and the 1,3-POD oxidoreductase-encoding gene may be yqhD or dhaT, or the 1,3-POD oxidoreductase-encoding gene derived from *E. coli* may be yqhD.

In another example of the present disclosure, a glycerol catabolic pathway was first constructed by introducing a glycerol facilitator, a glycerol kinase, and a glycerol-3-phosphate dehydrogenase. Through ALE, it could be confirmed that cell growth of the mutant strain significantly increased when glycerol was used as a single carbon source at an initial glycerol concentration of about 40 g/L.

Based on the above-described result, a strain showing excellent cell growth when using glycerol as a single carbon source was selected, and then a 1,3-PDO biosynthesis metabolic pathway was constructed by introducing glycerol dehydratase, glycerol reactivase and 1,3-PDO oxidoreductase into the selected strain. For about six mutant microorganisms in which the PDO biosynthesis metabolic pathway was constructed or enhanced, it was confirmed that the *Klebsiella pneumoniae* DSMZ2026-derived pduCDEGH gene encoding glycerol dehydratase and glycerol reactivase and the *E. coli*-derived yqhD gene encoding 1,3-PDO oxidoreductase produced the highest amount of 1,3-PDO.

From the above-described result, it could be confirmed that overexpression of glycerol dehydratase, glycerol reactivase and 1,3-PDO oxidoreductase enhanced the 1,3-PDO biosynthesis metabolic pathway and made 1,3-PDO production possible.

Therefore, in still another aspect, the present disclosure is directed to a method of producing 1,3-propanediol from glycerol, the method comprising steps of: (a) culturing, in a glycerol-containing medium, the mutant microorganism having the ability to produce 1,3-propanediol from glycerol, thereby producing 1,3-propanediol; and (b) collecting the produced 1,3-propanediol.

According to the present disclosure, glucose may be added to the medium, and the weight ratio between the glucose added to the medium and the glycerol may be 1:2 to 9.

In another example of the present disclosure, it could be confirmed that the ability to produce 1,3-PDO was the highest under certain micro-aerobic conditions, determined by optimizing the aeration conditions during strain culture. The constructed mutant microorganism, which shows excellent cell growth when using glycerol as a single carbon source and has imparted or enhanced ability to produce 1,3-PDO, was named MBEL-HCC-C-13PDO1.

In another embodiment of the present disclosure, fed-batch fermentation culture of the MBEL-HCC-C-13PDO1 strain was performed under optimized aeration conditions, including, but not particularly limited to, 0.25 vvm, 600 rpm, a pH of 7 and a temperature of 30° C. It was confirmed that, under these conditions, about 47.3 g/L of 1,3-PDO was produced when glycerol was used as a single carbon source. Under these conditions, about 44.0 g/L of 3-HP was observed as a by-product. Thus, it was determined that the endogenous activity of any aldehyde dehydrogenase enzyme naturally present in Corynebacterium glutamicum was created or enhanced to supply the reducing power required for the production of 1,3-PDO. Thus, in order to reduce the endogenous activity of the 3-HP production metabolic pathway by supplying the reducing power derived from the activation of the pentose phosphate pathway by adding a certain proportion of glucose, culture was performed using a specific ratio of glucose and glycerol as carbon sources. As a result, it was confirmed that, when glucose and glycerol were used at a specific ratio, the production of 3-HP decreased and the production of 1,3-PDO increased. This indicates that, when aldehyde dehydrogenase, which is involved in the 3-HP production metabolic pathway, is deleted or weakened in a microorganism showing the ability to produce 3-HP, among microorganisms imparted with the ability to produce 1,3-PDO, the ability of the microorganism to produce 1,3-PDO is enhanced.

Based on these results, it was determined that the addition of glucose enhanced the supply of reducing power, thus weakening the activity of aldehyde dehydrogenase, fed-batch fermentation culture was performed at the observed ratio, and as a result, it was confirmed that 60.3 g/L of 1,3-PDO was produced in the MBEL-HCC-C-13PDO1 strain. In addition, it was confirmed that, when the proportion of glucose was slightly increased to further increase the supply of reducing power and further weaken the activity of aldehyde dehydrogenase, and as a result, 77.3 g/L of 1,3-PDO was finally produced.

As used herein, the term "endogenous activity" refers to the activity of an enzyme that a microorganism possesses in its native state, namely in the state without modification, and the meaning of "modified to have enhanced activity compared to the endogenous activity" is that the activity of the enzyme is newly introduced or further improved compared to the activity of the corresponding enzyme before modification.

In the present disclosure, "enhancement of enzymatic activity" includes improvement in the enzymatic activity by improvement in endogenous gene activity, amplification of the endogenous gene by internal or external factors, deletion of a regulatory factor for suppressing the gene expression, increase in the gene copy number, increase in activity by introduction of a foreign gene or modification of an expression regulatory sequence, in particular, replacement or modification of a promoter and mutation within a gene, as well as introduction or improvement of the activity of the enzyme itself to achieve effects beyond the endogenous functions.

In the present disclosure, "modified to have enhanced activity compared to the endogenous activity" means that the activity of the microorganism is increased after manipulation such as introduction of a gene showing the activity, or increase in the gene copy number, deletion of a regulatory factor for suppressing the gene expression or modification of an expression regulatory sequence, for example, use of an improved promoter, compared to the activity of the microorganism before the manipulation.

In the present disclosure, "deletion" is meant to encompass mutation, substitution (replacement) or deletion of all or part of a target gene or the introduction of one or more nucleotides into the gene, so that the gene is not expressed or does not exhibit enzymatic activity, and further, so that, even though it is expressed, the gene-associated biosynthetic pathway is blocked.

In the present disclosure, "overexpression" refers to expression of a gene in a cell at a level higher than normally expressed in a cell of that type, and is meant to include increasing expression levels by a method of replacing the promoter of a gene present on the genome with a strong promoter or a method of cloning the relevant gene into an expression vector and transforming a cell with the expression vector.

In the present disclosure, "vector" refers to a DNA construct containing a DNA sequence which is operably linked to a suitable control sequence capable of effecting the expression of the DNA in a suitable host. The vector may be a plasmid, a phage particle, or simply a potential genomic insert. Once incorporated into a suitable host, the vector may replicate and function independently of the host genome, or may, in some instances, integrate into the genome itself. In the present specification, "plasmid" and "vector" are sometimes used interchangeably, as the plasmid is the most commonly used form of vector. For the purpose of the present disclosure, a plasmid vector is preferably used. A typical plasmid vector which may be used for this purpose contains: (a) a replication origin by which replication occurs efficiently such that several hundred plasmid vectors per host cell are created; (b) an antibiotic-resistant gene by which host cells transformed with the plasmid vector can be selected; and (c) restriction enzyme cutting sites into which foreign DNA fragments can be inserted. Even if suitable restriction enzyme cutting sites are not present in the vector, the use of a conventional synthetic oligonucleotide adaptor or linker enables easy ligation between the vector and the foreign DNA fragments.

After ligation, the vector should be transformed into suitable host cells. In the present disclosure, the preferred host cells are prokaryotic cells. Suitable prokaryotic host cells include E. coli DH5α, E. col JM101, E. coli K12, E. coli W3110, E. coli X1776, E. coli XL-1 Blue (Stratagene), E. coli B, and E. coli B21. However, E. coli strains such as FMB101, NM522, NM538 and NM539, as well as the species and genera of other prokaryotes, and the like, may also be used. In addition to the E. coli mentioned above, strains of the genus Agrobacterium, such as Agrobacterium A4, Bacillus strains such as Bacillus subtilis, other enterobacteria such as Salmonella typhimurium or Serratia marcescens, and various strains of the genus Pseudomonas may be used as host cells.

Transformation of prokaryotic cells may be easily carried out using a calcium chloride method described in Section 1.82 of Sambrook et al., supra. Alternatively, electroporation (Neumann, et al., EMBO J., 1: 841, 1982) may also be used for transformation of these cells.

The vector that is used for overexpression of the gene according to the present disclosure may be an expression vector known in the art, and is preferably a pET-based vector (Novagen). When cloning is performed using a pET-based vector, histidine groups are bonded to the ends of the expressed protein, and thus the protein can be effectively purified. A conventional method known in the art may be used to isolate the expressed protein from the cloned gene. Specifically, the expressed protein may be isolated through a chromatographic method using Ni-NTA His-conjugated resin (Novagen). In the present disclosure, the recombinant vector may be pET-SLTI66, and the host cell may be *E. coli* or *Agrobacterium*.

As used herein, the term "expression control sequence" means a DNA sequence essential for the expression of a coding sequence operably linked to a particular host organism. Such a control sequence includes promoters for conducting transcription, any operator sequences for controlling such transcription, sequences for encoding suitable mRNA ribosome-binding sites, and sequences for controlling the termination of transcription and translation. For example, control sequences suitable for prokaryotes include promoters, optionally operator sequences and ribosome binding sites. Eukaryotic cells include promoters, polyadenylation signals and enhancers. The factor that has the greatest impact on the expression level of a gene in a plasmid is a promoter. SRα promoters, cytomegalovirus-derived promoters and the like are preferably used as promoters for high expression. Any of a wide variety of expression control sequences may be used for the vector in order to express the DNA sequence of the present disclosure. Useful expression control sequences include, for example, the early and late promoters of SV40 or adenovirus, the lac system, the trp system, the TAC or TRC system, T3 and T7 promoters, the major operator and promoter regions of phage lambda, control regions of fd code proteins, promoters of 3-phosphoglycerate kinase or other glycol lyases, promoters of phosphatase, such as Pho5, promoters of yeast alpha-mating systems, or other sequences known to control gene expression of prokaryotic or eukaryotic cells or viruses, and various combinations thereof. The T7 promoter may be useful for expressing proteins of the present disclosure in *E. coli*.

When a nucleic acid sequence is aligned with another nucleic acid sequence based on a functional relationship, it is "operably linked" thereto. It may be gene(s) and control sequence(s) linked in such a way so as to enable gene expression when a suitable molecule (e.g., a transcriptional activator protein) is linked to the control sequence(s). For example, DNA for a pre-sequence or secretory leader is operably linked to DNA for a polypeptide when expressed as a pre-protein involved in the secretion of the polypeptide; and a promoter or enhancer is operably linked to a coding sequence when it affects the transcription of the sequence; or a ribosome-binding site is operably linked to a coding sequence when it affects the transcription of the sequence; or the ribosome-binding site is operably linked to a coding sequence when positioned to facilitate translation. Generally, "operably linked" means that the linked DNA sequence is in contact therewith, or that a secretory leader is in contact therewith and is present in the reading frame. However, the enhancer need not be in contact therewith. The linkage of these sequences is carried out by ligation (linkage) at convenient restriction enzyme sites. When no such site exists, a synthetic oligonucleotide adapter or a linker according to a conventional method is used.

As used herein, the term "expression vector" commonly refers to a recombinant carrier into which a fragment of heterologous DNA is inserted, and generally means a fragment of double-stranded DNA. Here, the heterologous DNA refers to exogenous DNA that is not naturally found in a host cell. Once an expression vector is present in a host cell, it can replicate independently of the host chromosomal DNA, and several copies of the vector and inserted (heterologous) DNA thereof can be produced.

As is well known in the art, in order to increase the expression level of a transgene in a host cell, the gene should be operably linked to a transcriptional/translational expression control sequence that functions in a selected expression host. Preferably, the expression control sequence and the corresponding gene are included in one recombinant vector containing both a bacterial selection marker and a replication origin. When the host cell is a eukaryotic cell, the recombinant vector should further include a useful expression marker in the eukaryotic expression host.

The host cell transected or transformed by the recombinant vector described above constitutes another aspect of the present disclosure. As used herein, the term "transformation" means introducing DNA into a host and making the DNA replicable using an extrachromosomal factor or chromosomal integration. As used herein, the term "transfection" means that an expression vector is accommodated by the host cell, regardless of whether or not any coding sequence is actually expressed.

It should be understood that not all vectors function equally to express the DNA sequences of the present disclosure. Similarly, not all hosts function equally with respect to the same expression system. However, any person skilled in the art may appropriately select from among various vectors, expression control sequences, and hosts without either departing from the scope of the present disclosure or bearing excessive experimental burden. For example, a vector should be selected in consideration of a host, because the vector should be replicated in the host. In addition, the number of copies of the vector, the ability to regulate the number of copies and the expression of other proteins encoded by the corresponding vector (e.g., the expression of an antibiotic marker) should also be considered. An expression control sequence should be selected considering a number of factors. For example, the relative strength of the sequence, controllability, and compatibility with the DNA sequences of the present disclosure should be considered, particularly in relation to possible secondary structures. A single cell host may be selected in consideration of factors such as the selected vector, the toxicity of the product encoded by the DNA sequence of the present disclosure, secretion characteristics, the ability to accurately fold proteins, culture and fermentation factors, and ease of purification of the product encoded by the DNA sequence according to the present disclosure. Within the scope of these factors, those skilled in the art can select various vector/expression control sequences/host combinations capable of expressing the DNA sequences of the present disclosure in fermentation or large animal cultures. As a screening method for cloning the cDNA of the protein according to the present disclosure through expression cloning, it is possible to apply a binding method, a panning method, a film emulsion method or the like.

Hereinafter, the present disclosure will be described in more detail with reference to the following examples. However, it will be obvious to those skilled in the art that the following examples are provided merely to illustrate the present disclosure and should not be construed as limiting the scope of the present disclosure.

In the following examples, *Corynebacterium glutamicum* was used as a host microorganism. However, it will be obvious to those skilled in the art that other kinds of *E. coli*, bacteria, yeasts and fungi may also be used. In addition, although only genes derived from a specific strain are illustrated as the genes to be introduced in the following examples, it will be obvious to those skilled in the art that these genes are not limited, as long as they are capable of being expressed in a host cell and exhibit desired activities.

EXAMPLE 1

Construction of Recombinant *Corynebacterium glutamicum* Capable of Growing Using Glycerol as Single Carbon Source 1-1: Construction of pCSglpFKD Vector for Construction of Glycerol Catabolic Pathway It is known that cells of *Corynebacterium glutamicum* are incapable of growing using glycerol as a single carbon source. Thus, in order to construct the glycerol catabolic pathway, the *E. coli* W3110-derived genes encoding the enzymes responsible for the glycerol catabolic pathway were first expressed using the *Corynebacterium glutamicum* shuttle vector pCES208s-H36-S3.

Figure 2:
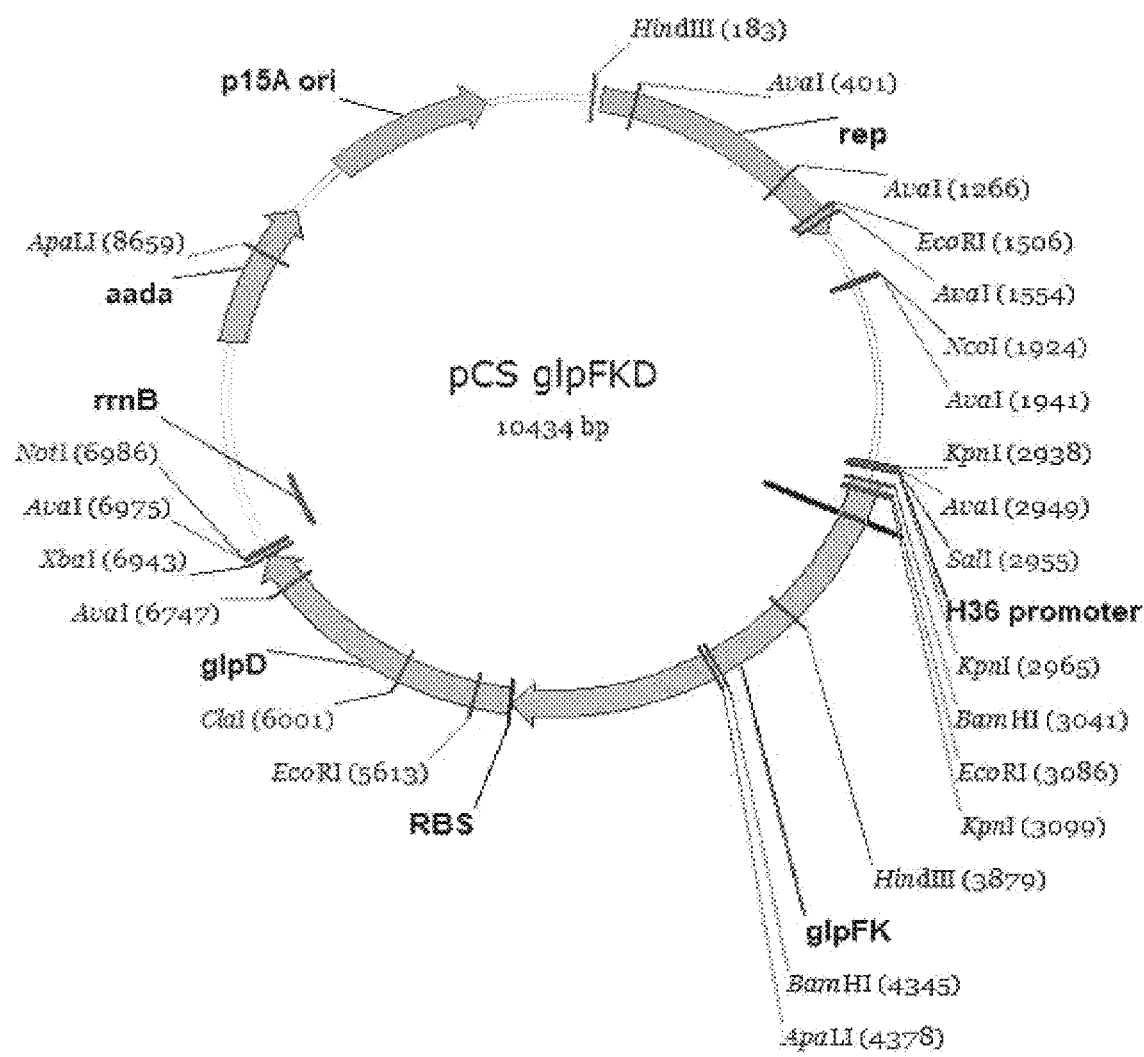
FIG. 2 shows a pCSglpFKD recombinant vector containing glpF, glpK and glpD genes that encode the glycerol catabolic pathway.

A glpFK gene fragment encoding glycerol facilitator and glycerol kinase operon enzymes was obtained by performing PCR using the chromosomal DNA of *E. coli* W3110 (ATCC 39936) as a template and the primers of SEQ ID NOs: 1 and 2, and a glpD gene fragment encoding glycerol-3-phosphate dehydrogenase was obtained by performing PCR using the primers of SEQ ID NOs: 3 and 4. To ligate the glpFK gene fragment (SEQ ID NO: 19) with the glpD gene fragment (SEQ ID NO: 20), overlapping PCR was performed using the primers of SEQ ID Nos: 1 and 4 to obtain a glpFKD gene fragment. To linearize a pCES208s-H36-S3 vector (a vector (SEQ ID NO: 21) obtained by substituting the Km antibiotic of a pCES208-H36 vector (Korean Patent Application Laid-Open Publication No. 10-2013-0022691 or Yim S. S. et al., Biotechnol. Bioeng., 110:2959, 2013) with a spectinomycin antibiotic), PCR was performed using the primers of SEQ ID NOs: 5 and 6. A pCSglpFKD vector was constructed by ligating the linearized vector with the constructed glpFKD gene fragment using a Gibson assembly method (FIG. 2).

First, the recombinant strain library having the glpFKD gene introduced therein was inoculated into a test tube containing 10 mL of BHIS medium (37 g/L Brain Heart Infusion (BHI) and 91 g/L sorbitol) and pre-cultured at 30° C. for 16 hours. Then, 1 mL of the pre-culture was inoculated and cultured in 25 mL of a CGXII medium (Table 2) in a 250-mL baffle flask. The initial glycerol concentration of the medium was set to 10 g/L, 20 g/L and 40 g/L, and flask culture was performed in triplicate for 48 hours.

Figure 3:
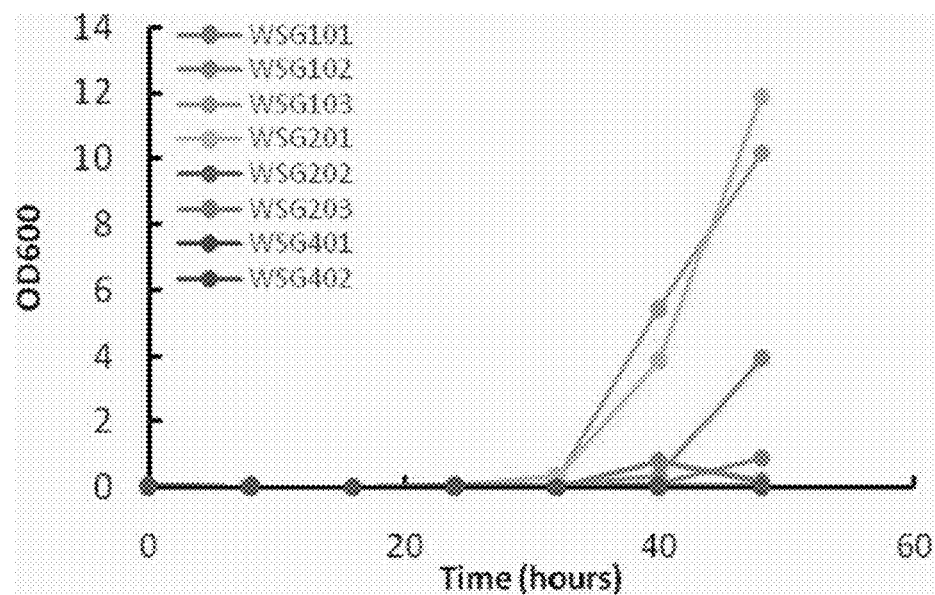
FIG. 3 shows the results of observing cell growth at initial glycerol concentrations of 18 g/L, 20 g/L and 40 g/L during flask culture of a wild-type Corynebacterium glutamicum ATCC13032 strain having a pCSglpFKD vector introduced therein.

As a result, as shown in FIG. 3, all of the strains in the recombinant strain library had a very long lag phase. Among the strains cultured at an initial glycerol concentration of 20 g/L, the WSG201 strain showing the fastest cell growth was selected. To increase the glycerol uptake rate of the selected WSG201 strain, Adaptive Laboratory Evolution (ALE) was performed.

Figure 4:
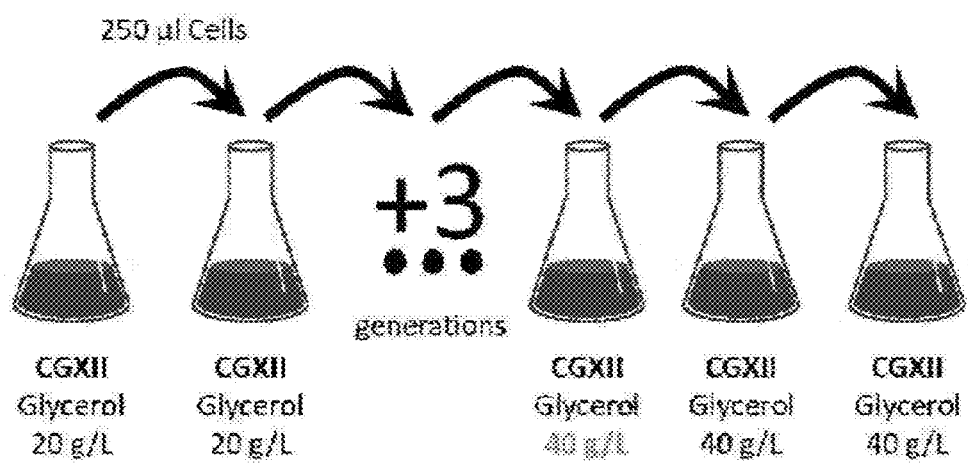
FIG. 4 is a schematic view showing an ALE method performed at an initial glycerol concentration ranging from 20 g/L to 40 g/L using a wild-type Corynebacterium glutamicum ATCC13032 strain having a pCSglpFKD vector introduced therein.

As shown in FIG. 4, ALE was performed by inoculating and culturing 250 µL of a preculture in 25 mL of CGXII medium in a 250-mL flask. ALE was performed for a total of eight generations starting with an initial glycerol concentration of 20 g/L, and an initial glycerol concentration of 40 g/L was used from the fifth generation.

Figure 5:
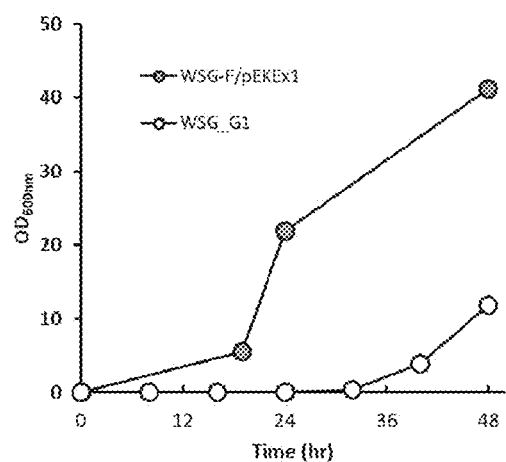
FIG. 5 shows that the cell growth rate of the wild-type Corynebacterium glutamicum ATCC13032 strain having a pCSglpFKD vector introduced therein significantly increases at an initial glycerol concentration of 40 g/L in flask culture through the ALE method.

As a result, as shown in FIG. 5, it could be confirmed that the lag phase of the strain, which was very long when cultured in the glucose-containing medium, significantly decreased, and cell growth of the strain also increased. That is, from the results of ALE, it can be seen that, at an initial glycerol concentration of 40 g/L, the lag phase of the transformed recombinant strain significantly decreased and cell growth thereof was significantly enhanced.

TABLE 2

| CGXII medium composition used in culture of *Corynebacterium glutamicum* | |
|---|---|
| Components of CGXII-glycerol medium | Concentrations |
| $CaCl_2 \cdot 2H_2O$ | 13 mg/L |
| $FeSO_{40} \cdot 7H_2O$ | 10 mg/L |
| $MnSO_4 \cdot 5H_2O$ | 14 mg/L |
| $ZnSO_4 \cdot 7H_2O$ | 1 mg/L |
| $CuSO_4 \cdot 5H_2O$ | 300 µg/L |

TABLE 1

Primers for construction of pCSglpFKD vector

| SEQ ID NO | Nucleotide sequence |
|---|---|
| SEQ ID NO: 1 | 5'-TTGGTTGGTAGGAGTAGCATGGGATCCATGAGTCAAACATCAACCTT-3' |
| SEQ ID NO: 2 | 5'-GTTTCCATCTATATCTCCTTTTATTCGTCGTGTTCTTCCC-3' |
| SEQ ID NO: 3 | 5'-AAGGAGATATAGATGGAAACCAAAGATCTGAT-3'' |
| SEQ ID NO: 4 | 5'-TAATTATAATGGCCGGCTGGGCCTCTAGAGTTACGACGCCAGCGATAACC-3'' |
| SEQ ID NO: 5 | 5'-TCTAGAGGCCCAGCCGGCCATTATAATTAG-3' |
| SEQ ID NO: 6 | 5'-GGATCCCATGCTACTCCTACCAACCAAGGT-3' |

1-2: Construction of Recombinant *Corynebacterium glutamicum* and Enhancement of Bacterial Growth by Glycerol Degradation A recombinant strain library having the glpFKD gene introduced therein was constructed by introducing the pCSglpFKD vector, constructed in Example 1-1, into a wild-type *Corynebacterium glutamicum* ATCC13032 strain, and flask culture was performed using glycerol as a carbon source in order to confirm cell growth resulting from glycerol degradation.

TABLE 2-continued

CGXII medium composition used in culture
of *Corynebacterium glutamicum*

| Components of CGXII-glycerol medium | Concentrations |
|---|---|
| NiCl$_2$ · 6H$_2$O | 20 µg/L |
| (NH$_4$)$_2$SO$_4$ | 20 g/L |
| Urea | 2 g/L |
| KH$_2$PO$_4$ | 1 g/L |
| K$_2$HPO$_4$ | 1 g/L |
| Biotin | 200 µg/L |
| Thiamine | 500 µg/L |
| Protocatechuic Acid | 30 mg/L |
| MOPS | 42 g/L |
| Glycerol | 10 g/L, 20 g/L, 40 g/L |
| Spectinomycin | 200 µg/L |

EXAMPLE 2

Analysis and Optimization of 1,3-PDO Production in Recombinant *Corynebacterium glutamicum* when Using Glycerol as Single Carbon Source 2-1: Construction of pEK-dgyE, pEK-dgyK, pEK-dgdk, pEK-pduyE, pEK-pduyk and pEK-pdudk Vectors for Construction of 1,3-PDO Biosynthesis Metabolic Pathway In order to construct the 1,3-PDO biosynthesis metabolic pathway in the recombinant *Corynebacterium glutamicum* whose cells were confirmed to grow using glycerol as a single carbon source in Example 1-2, exogenous enzymes derived from *Klebsiella pneumoniae* DSMZ2026 (KCTC 4952) and *E. coli* W3110 were expressed using a *Corynebacterium glutamicum* pEKEx1 shuttle vector (Eikmanns et al., Gene 102: 93, 1991; SEQ ID NO: 22).

Figure 6:
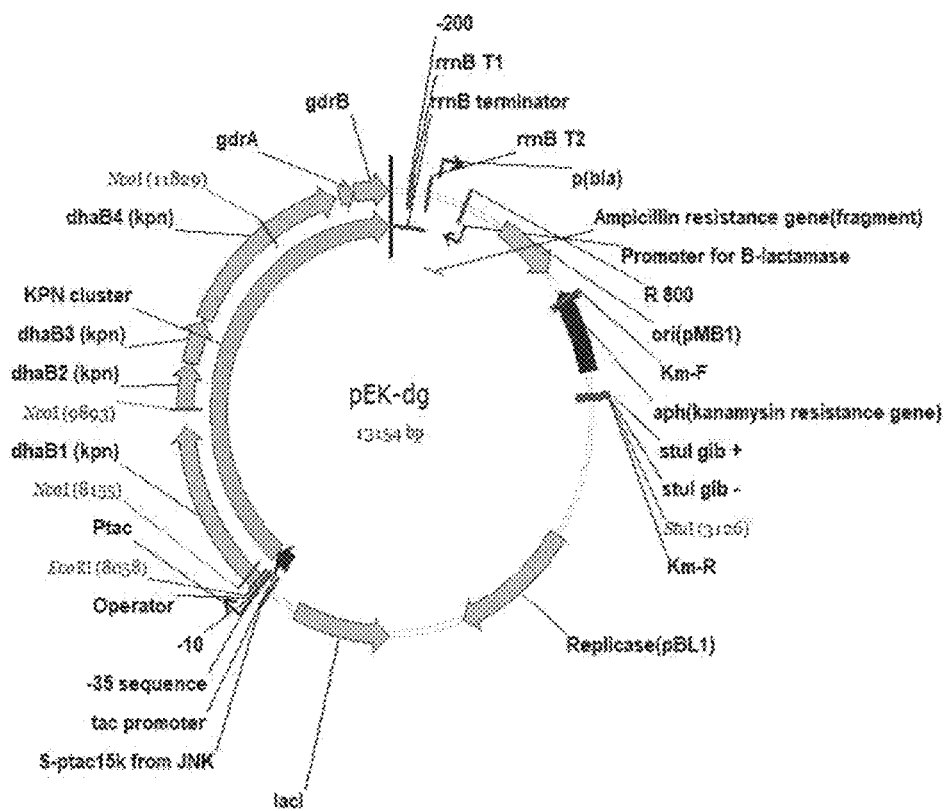
FIG. 6 shows a pEK-dg recombinant vector constructed by inserting a dhaB1234/gdrAB gene cluster encoding glycerol dehydratase and glycerol reactivase to construct a 3-HPA biosynthesis metabolic pathway.
Figure 7:
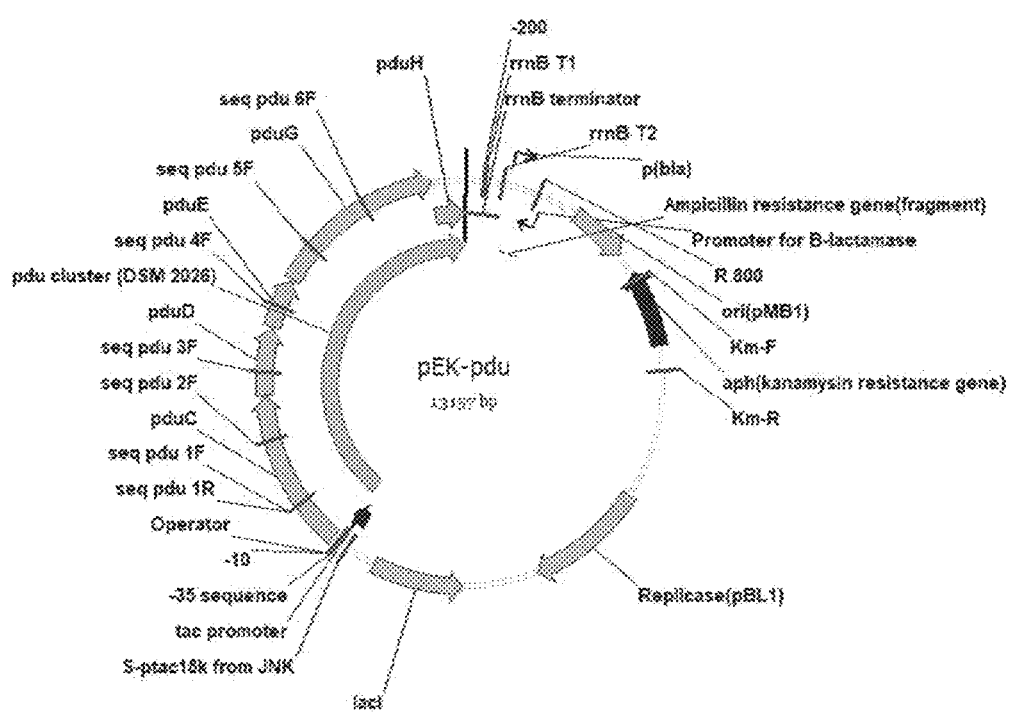
FIG. 7 shows a pEK-pdu recombinant vector constructed by inserting a pduCDEGH gene cluster encoding glycerol dehydratase to construct a 3-HPA biosynthesis metabolic pathway.

First, a dhaB1234/gdrAB gene cluster fragment encoding glycerol dehydratase and glycerol reactivase was obtained by performing PCR using the chromosomal DNA of a *Klebsiella pneumoniae* DSMZ2026 strain as a template and the primers of SEQ ID NOs: 7 and 8. In addition, a pduCDEGH gene cluster fragment encoding another glycerol dehydratase and glycerol reactivase was obtained by performing PCR using the chromosomal DNA of a *Klebsiella pneumoniae* DSMZ2026 strain as a template and the primers of SEQ ID NOs: 9 and 10. To ligate each of the obtained dhaB1234/gdrAB gene fragment and pduCDEGH gene fragment to the shuttle vector pEKEx1 vector, the gene fragments were treated with the restriction enzymes EcoRI and PstI and then ligated to the shuttle vector by Gibson assembly, thereby constructing a pEK-dg vector (FIG. 6) and a pEK-pdu vector (FIG. 7), respectively.

A yqhD gene fragment encoding 1,3-PDO oxidoreductase was obtained by performing PCR using a pTac15kyqhD recombinant vector (a recombinant vector obtained by inserting *E. coli* W3110-derived yqhD into a pTac15k vector (p15A origin, tac promoter, Km$^R$); SEQ ID NO: 23) as a template and the primers of SEQ ID NOs: 11 and 12, and yqhD gene and dhaT gene fragments were obtained by performing PCR using the chromosomal DNA of a *Klebsiella pneumoniae* DSMZ2026 strain as a template and the primers of SEQ ID NOs: 11 and 13 and the primers of SEQ ID NOs: 11 and 14, respectively.

Figure 8:
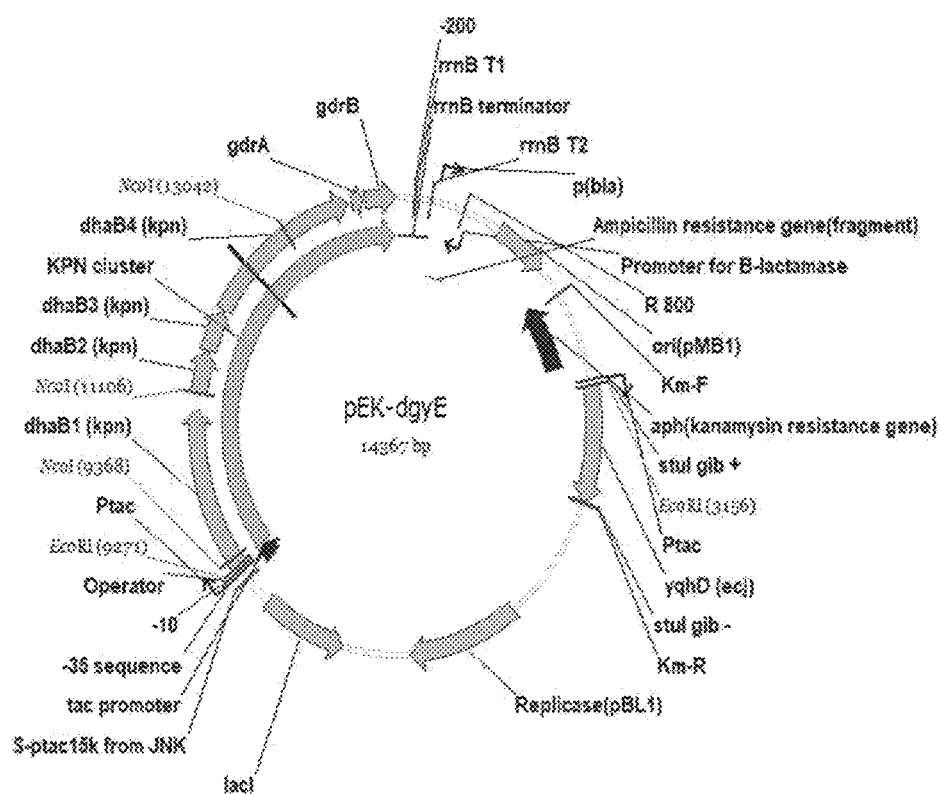
FIG. 8 shows a pEK-dgyE recombinant vector constructed by inserting a yqhD gene encoding E. coli 1,3-PDO oxidoreductase into a pEK-dg vector to construct a 1,3-PDO biosynthesis metabolic pathway.
Figure 9:
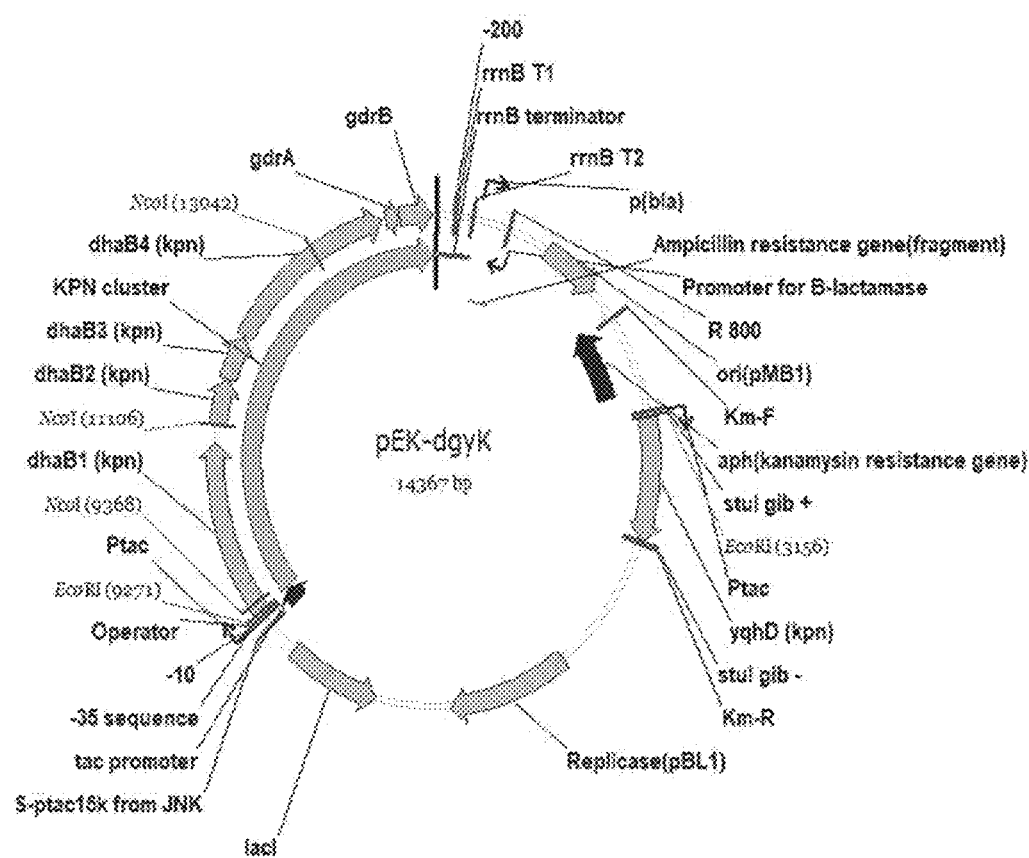
FIG. 9 shows a pEK-dgyE recombinant vector constructed by inserting an yqhD gene encoding Klebsiella pneumoniae DSMZ2026 1,3-PDO oxidoreductase into a pEK-dg vector to construct a 1,3-PDO biosynthesis metabolic pathway.
Figure 10:
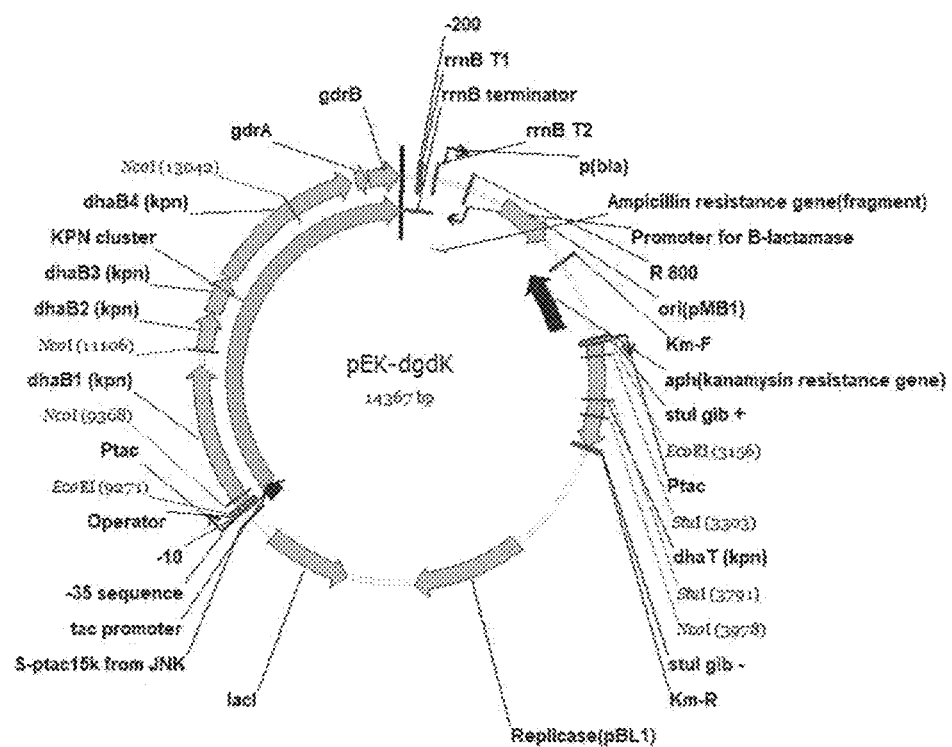
FIG. 10 shows a pEK-dgyE recombinant vector constructed by inserting a dhaT gene encoding Klebsiella pneumoniae DSMZ2026 1,3-PDO oxidoreductase into a pEK-dg vector to construct a 1,3-PDO biosynthesis metabolic pathway.

To ligate each of the obtained gene fragments to a pEK-dg vector, the gene fragments were ligated with the restriction enzyme StuI and ligated to the vector by Gibson assembly, thereby constructing a pEK-dgyE vector (FIG. 8), a pEK-dgyK vector (FIG. 9) and a pEK-dgdK vector (FIG. 10), respectively.

A yqhD gene fragment encoding 1,3-PDO oxidoreductase was obtained by performing PCR using the pTac15kyqhD recombinant vector as a template and the primers of SEQ ID NOs: 15 and 16, and yqhD and dhaT gene fragments encoding another 1,3-PDO oxidoreductase were obtained by performing PCR using the chromosomal DNA of a *Klebsiella pneumoniae* DSMZ2026 strain as a template and the primers of SEQ ID NOs: 15 and 17 and the primers of SEQ ID NOs: 15 and 18, respectively.

Figure 11:
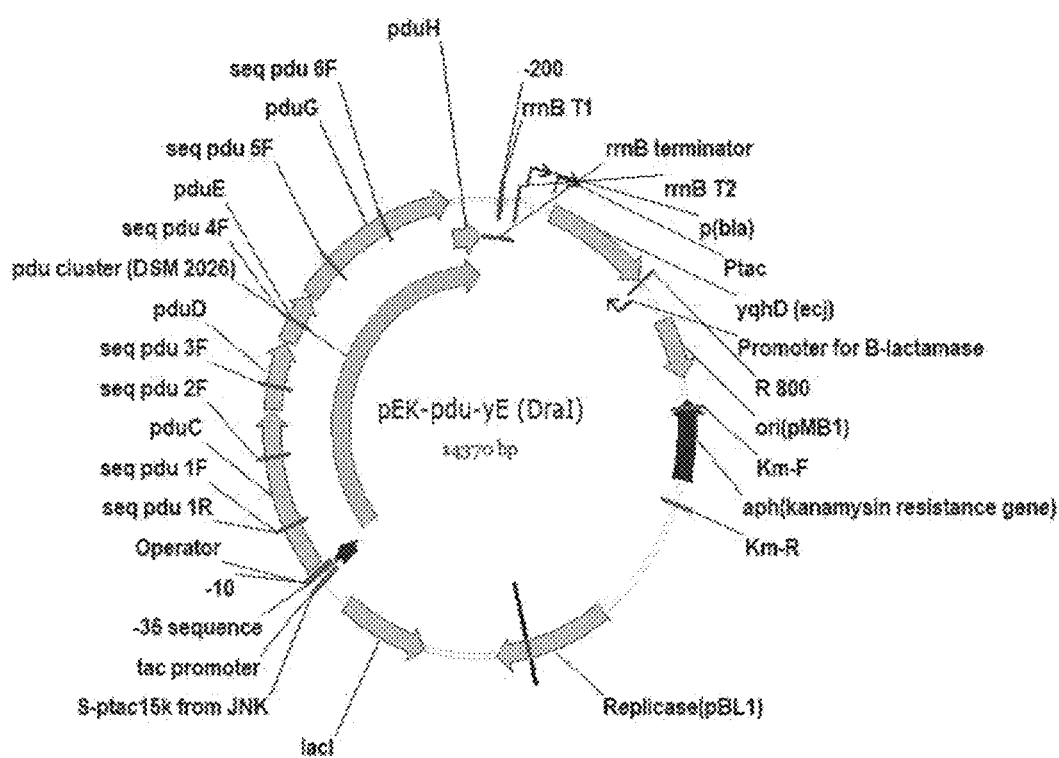
FIG. 11 shows a pEK-pduyE recombinant vector constructed by inserting a yqhD gene encoding E. coli 1,3-PDO oxidoreductase into a pEK-pdu vector to construct a 1,3-PDO biosynthesis metabolic pathway.
Figure 12:
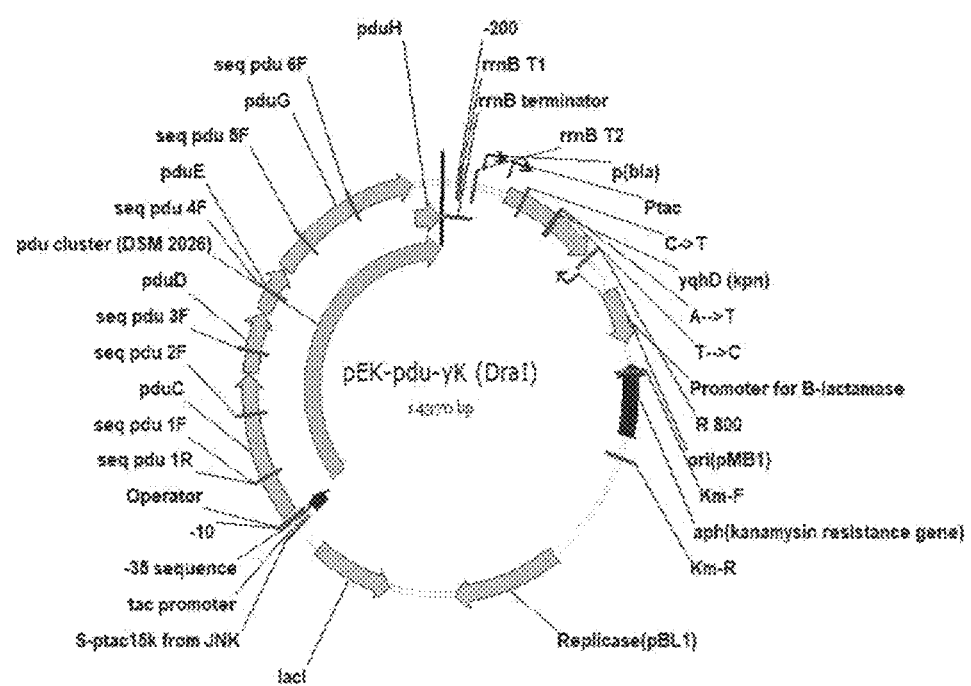
FIG. 12 shows a pEK-pduyE recombinant vector constructed by inserting a yqhD gene encoding Klebsiella pneumoniae DSMZ2026 1,3-PDO oxidoreductase into a pEK-pdu vector to construct a 1,3-PDO biosynthesis metabolic pathway.
Figure 13:
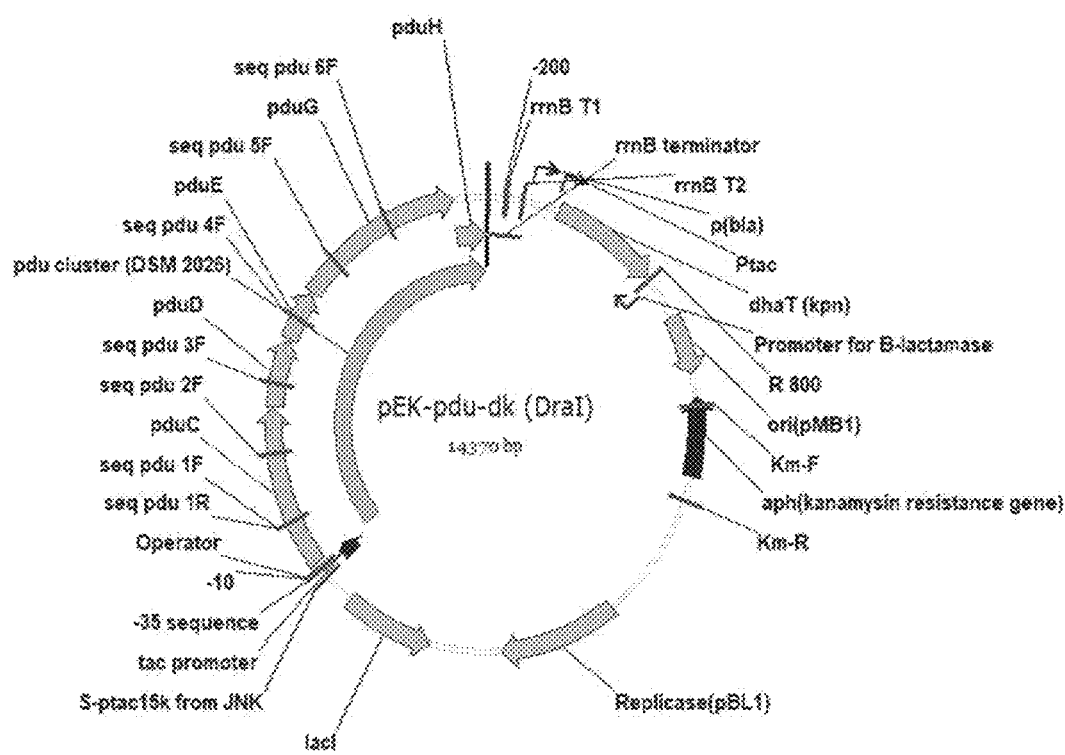
FIG. 13 shows a pEK-pduyE recombinant vector constructed by inserting a dhaT gene encoding Klebsiella pneumoniae DSMZ2026 1,3-PDO oxidoreductase into a pEK-pdu vector to construct a 1,3-PDO biosynthesis metabolic pathway.

To ligate each of the obtained gene fragments to a pEK-pdu vector, the gene fragments were treated with the restriction enzyme DraI and ligated to the vector by Gibson assembly, thereby constructing a pEK-pduyE vector (FIG. 11), a pEK-pduyK vector (FIG. 12) and a pEK-pdudK vector (FIG. 13), respectively.

TABLE 3

Primers for construction of recombinant vectors comprising 1,3-PDO biosynthesis metabolic pathway

| SEQ ID NO | Nucleotide Sequence |
|---|---|
| SEQ ID NO: 7 | 5'-ACAATTTCACACAGGAAACAGAATTCATGAAAAGATCAAAAC-3' |
| SEQ ID NO: 8 | 5'-AAAACAGCCAAGCTTGGCTGCAGTCAGTTTCTCTCACTTAACG-3'' |
| SEQ ID NO: 9 | 5'-ACAATTTCACACAGGAAACAGAATTCATGAGATCGAAAAGATTTGAAG-3' |
| SEQ ID NO: 10 | 5'-AAAACAGCCAAGCTTGGCTGCAGTTAAGCATGGCGATCCCGAAATG-3'' |
| SEQ ID NO: 11 | 5'-TGGATGATGGGGCGATTCAGGTTGACAATTAATCATCGGCT-3' |
| SEQ ID NO: 12 | 5'-AAGGTGTTGCTGACTCATACCAGGTTAGCGGGCGGCTTCGTATA-3' |
| SEQ ID NO: 13 | 5'-AAGGTGTTGCTGACTCATACCAGGTTAGCGTGCAGCCTCGTAAA-3' |
| SEQ ID NO: 14 | 5'-AAGGTGTTGCTGACTCATACCAGGTCAGAATGCCTGGCGGAAAA-3' |
| SEQ ID NO: 15 | 5'-TTCCAATGATGAGCACTTTTTTGACAATTAAT-3' |

TABLE 3-continued

Primers for construction of recombinant vectors comprising 1,3-PDO biosynthesis metabolic pathway

| SEQ ID NO | Nucleotide Sequence |
|---|---|
| SEQ ID NO: 16 | 5'-GCGCCACATAGCAGAACTTTTTAGCGGGCGGCTTCGTATATAC-3' |
| SEQ ID NO: 17 | 5'-GCGCCACATAGCAGAACTTTTTAGCGTGCAGCCTCGTAAATAC-3' |
| SEQ ID NO: 18 | 5'-GCGCCACATAGCAGAACTTTTCAGAATGCCTGGCGGAAAAT-3' |

2-2: Construction of Mutant Microorganisms that Produce 1,3-PDO from Glycerol

Each of the six constructed recombinant vectors (pEK-dgyE, pEK-dgyK, pEK-dgdk, pEK-pduyE, pEK-pduyK and pEK-pdudK) was introduced into the recombinant strain (showing a significantly decreased lag phase and enhanced cell growth at an initial glycerol concentration of 40 g/L through ALE) obtained in Example 1-2, and then selection was performed in BHIS flat medium (37 g/L Brain Heart Infusion (BHI), 91 g/L sorbitol, and 15 g/L agar) supplemented with 25 μg/L kanamycin.

Each of the six selected recombinant strains was inoculated into a test tube containing 10 mL BHIS medium (37 g/L Brain Heart Infusion (BHI), and 91 g/L sorbitol) and pre-cultured at 30° C. for 16 hours, and then 1 mL of each of the pre-cultures was inoculated and cultured in 25 mL of CGXII medium in a 250-mL baffle flask. The initial glycerol concentration was set to 40 g/L, 10 g/L yeast extract was added to the medium, and flask culture was performed in triplicate for 48 hours.

Figure 14:
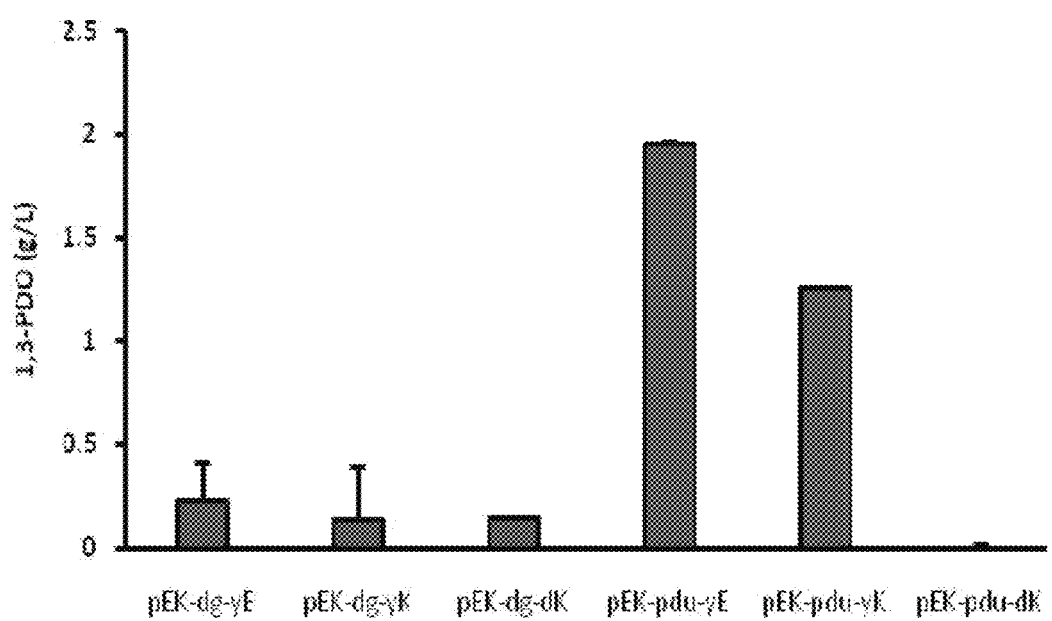
FIG. 14 shows the results of 1,3-PDO production observed in flask culture of Corynebacterium glutamicum mutant microorganisms introduced with six recombinant vectors (pEK-dgyE, pEK-dgyK, pEK-dgdK, pEK-pduyE, pEK-pduyK, and pEK-pdudK), respectively, to construct a 1,3-PDO biosynthesis pathway.

As a result, as shown in FIG. 14, it was confirmed that the recombinant strain having the pEK-pduyE vector introduced therein produced the highest amount of 1,3-PDO using glycerol as a single carbon source. The corresponding strain was named MBEL-HCC-C-13PDO1.

2-3: Optimization of Flask Culture Conditions for Increased Production of 1,3-PDO After 1,3-PDO production ability together with cell growth when using glycerol as a single carbon source was confirmed in Example 2-2, flask culture conditions were optimized to enhance 1,3-PDO production.

Since the activation concentrations of glycerol dehydratase and 1,3-PDO oxidoreductase involved in the 1,3-PDO biosynthesis metabolic pathway are known to be sensitive (inversely proportional) to the concentration of oxygen, aeration conditions, including the type of flask and the type of lid that seals the flask, were changed, and flask culture was performed.

First, the MBEL-HCC-C-13PDO1 strain was inoculated into a test tube containing 10 mL of BHIS medium and pre-cultured at 30° C. for 16 hours, and then 1 mL of the pre-culture was inoculated and cultured in 25 mL of CGXII medium in a 250-mL baffle flask or a 250-mL Erlenmeyer flask. The initial glycerol concentration was set to 40 g/L, 10 g/L of yeast extract was added to the medium, and flask culture was performed in triplicate for 48 hours. In this case, a baffle flask and an Erlenmeyer flask with relatively low aeration were selected as the types of flask, and a cotton lid and a sili-stopper with relatively low aeration were selected as the types of lid.

Figure 15:
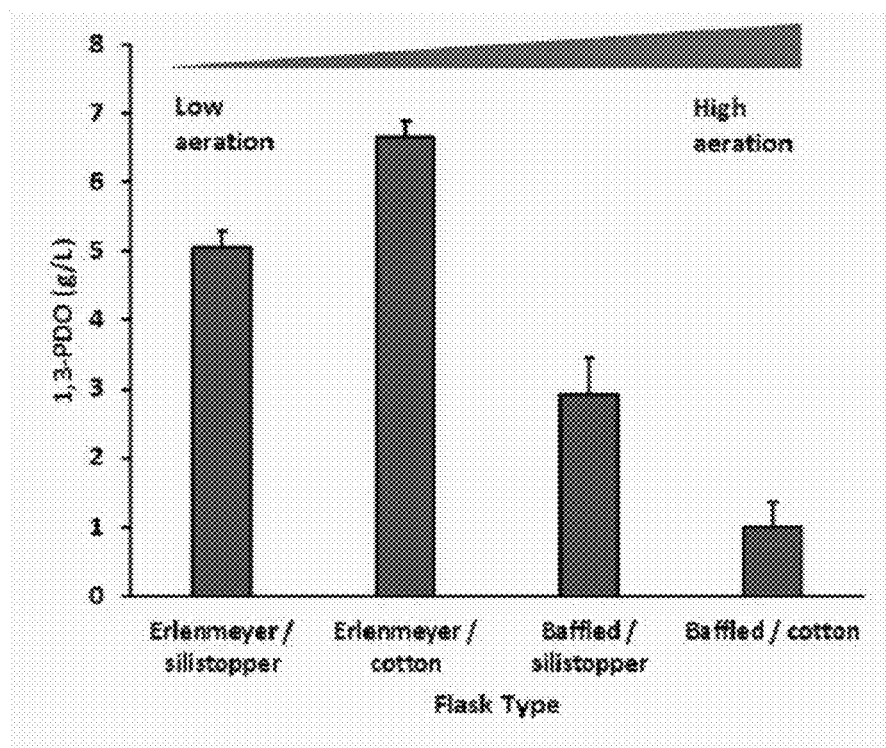
FIG. 15 shows the results of 1,3-PDO production by a MBEL-HCC-C-13PDO1 strain depending on aeration conditions in flask culture.

As a result, as shown in FIG. 15, it was confirmed that the MBEL-HCC-C-13PDO1 strain produced the largest amount of 1,3-PDO when the Erlenmeyer flask and the cotton lid were used (slightly micro-aerobic condition). This result indicates that the two enzymes involved in the 1,3-PDO biosynthesis metabolic pathway are influenced by aeration conditions and that 1,3-PDO production increases under the optimized aeration conditions.

2-4: Mutant Microorganism that Produces 1,3-PDO Through Fed-Batch Fermentation Culture Using the flask type and aeration conditions established in Example 2-3, fed-batch culture was performed to examine the 1,3-PDO production ability of the MBEL-HCC-C-13PDO1 strain.

First, the MBEL-HCC-C-13PDO1 strain was plated on a BHIS plate medium (37 g/L Brain Heart Infusion (BHI), 91 g/L sorbitol, and 15 g/L agar) supplemented with kanamycin and spectinomycin, and was cultured at 30° C. for 48 hours. The formed colony was inoculated into 50 mL of BHIS medium in the 250-mL Erlenmeyer flask having the cotton lid, selected in Example 2-3. Then, the colony was pre-cultured at 30° C. for 16 hours. The pre-culture was inoculated in 50 mL of CGXII medium ($OD_{600}$ at the start of culture=0.1) in each of four 250-mL baffle flasks (fermenter seed), and cultured in a shaking incubator at 200 rpm and 30° C. for 24 hours. Here, the initial glycerol concentration of the CGXII medium was set to 40 g/L, 10 g/L of yeast extract was added to the medium, and MOPS was excluded. Thereafter, a total of 200 mL of the pre-culture was inoculated into 1.8 L of a CGXII fermentation medium (a fermenter with a total volume of 6 L) (start $OD_{600}$=3.0 to 4.0), glycerol was added at an initial glycerol concentration of 40 g/L, 10 g/L of yeast extract was added, and MOPS was excluded. In addition, each of $MgSO_4$-$7H_2O$, biotin, thiamine, protocatechuic acid, kanamycin and spectinomycin was added after filtration. In addition, 1 mM IPTG was added at the first feeding at the end of the batch period.

During fed-batch fermentation culture, the pH was maintained at 7.0 using ammonia water (28%, Junsei Chemical Co., Ltd., Tokyo, Japan), and the temperature and the agitation speed were maintained at 30° C. and 600 rpm, respectively, in the P-I-D (proportional-integral-derivative) mode. The aeration rate was maintained at 0.25 vvm, and bubbles generated during culture were treated with antifoam 204 (Sigma-Aldrich). The feeding solution was composed of 800 g/L of glycerol, and when the residual glycerol concentration decreased to 10 g/L, 100 mL of the feeding solution was added.

Figure 16:
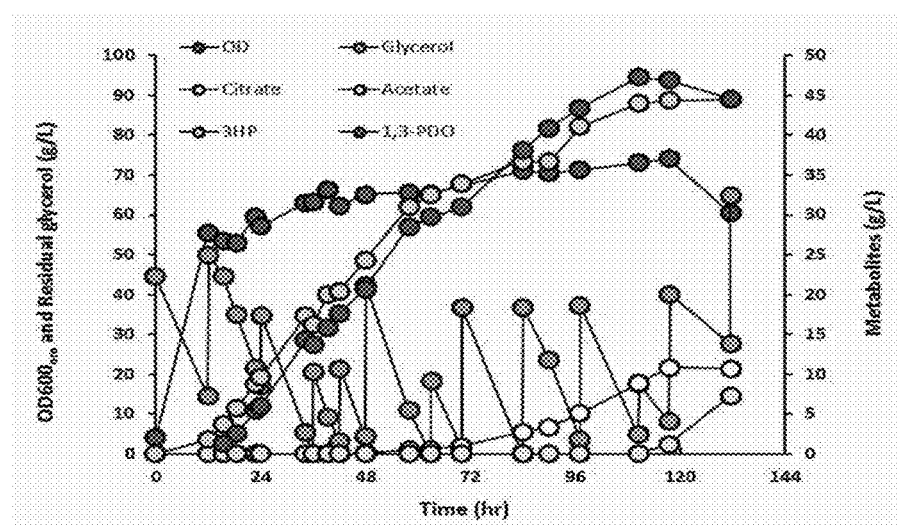
FIG. 16 shows the results of fed-batch fermentation culture of the MBEL-HCC-C-13PDO1 strain when using glycerol as a single carbon source.

As a result, as shown in FIG. 16, it was confirmed that, when fed-batch fermentation culture of the MBEL-HCC-C-13PDO1 strain was performed, about 47.3 g/L of 1,3-PDO was produced using glycerol as a single carbon source. Thus, it was confirmed that the MBEL-HCC-C-13PDO1 strain with the constructed glycerol catabolic pathway and 1,3-PDO biosynthesis metabolic pathway is capable of producing 1,3-PDO while the cells grow.

EXAMPLE 3

Increased Production of 1,3-PDO in Recombinant *Corynebacterium glutamicum* by Use of Glycerol and Glycerol as Carbon Sources 3-1: Increased Production of 1,3-PDO in *Corynebacterium glutamicum* through Optimization of Glycerol/Glucose Ratio As can be seen from the results of the fed-batch fermentation culture performed in Example 2-4, the MBEL-HCC-C-13PDO1 strain produced the highest amount of 1,3-PDO using glycerol as a single carbon source while the cells grew. However, it was shown that, under the above-described conditions, 3-HP was produced as a by-product in an amount similar to the amount of 1,3-PDO.

Considering redox balance, when the enzymes involved in the 1,3-PDO biosynthesis metabolic pathway and the 3-HP biosynthesis metabolic pathway use NADPH as a cofactor, it was determined that aldehyde dehydrogenase enzymes present in *Corynebacterium glutamicum* activated the 3-HP biosynthesis metabolic pathway to supply the reducing power NADPH required for 1,3-PDO production (FIG. 1). Thus, it was determined that, when glycerol was used as a single carbon source, the pentose phosphate metabolic pathway could not be used, and therefore the 3-HP biosynthesis metabolic pathway was further activated to increase the supply of NADPH (FIG. 1).

Since *Corynebacterium glutamicum* is known to supply about 70% of NADPH through the pentose phosphate metabolic pathway, a comparative experiment on flask culture was performed in order to examine whether the addition of glucose increases the production of 1,3-PDO.

First, the MBEL-HCC-C-13PDO1 strain was inoculated into a tube containing 10 mL of BHIS medium and was pre-cultured at 30° C. for 16 hours, and then 1 mL of the pre-culture was inoculated and cultured in 25 mL of CGXII in a 250-mL Erlenmeyer flask. Glucose and glycerol were added at initial weight ratios of 1:1, 1:3, 1:9 and 1:19, 10 g/L of yeast extract was added to the medium, and flask culture was performed in triplicate for 48 hours.

Figure 17:
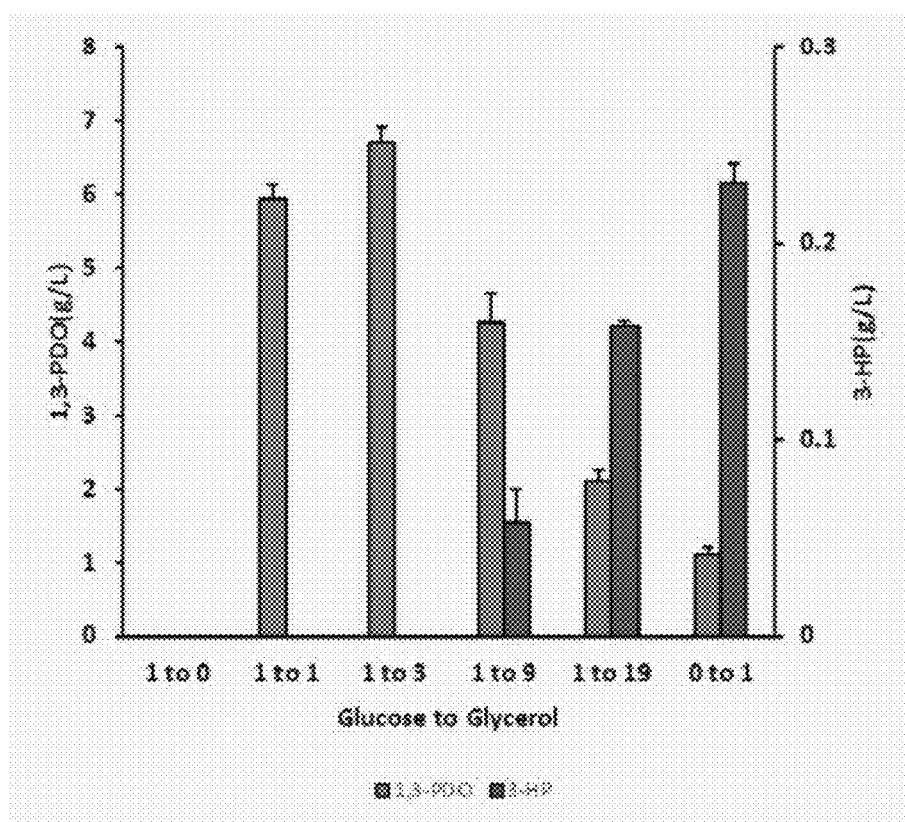
FIG. 17 shows the results of 1,3-PDO production observed in flask culture of the MBEL-HCC-C-13PDO1 strain depending on the weight ratio of glucose to glycerol.

As a result, as shown in FIG. 17, it was confirmed that, when glucose and glycerol were used at a weight ratio of 1:3, the 3-PDO production of the strain was the highest, and 3-HP was not produced. In addition, it was confirmed that, as the ratio of glycerol to glucose increased (as the amount of glucose decreased), 3-HP production increased, and as the ratio of glycerol to glucose decreased (as the amount of glucose increased), 3-HP production decreased. That is, these results indicate that, when the MBEL-HCC-C-13PDO1 strain uses glycerol as a single carbon source, the reducing power required for 1,3-PDO production is supplied by activating the 3-HP biosynthesis metabolic pathway, and that a specific ratio of glycerol to glucose is effective for increased production of 1,3-PDO.

3-2: Mutant Microorganism that Produces 1,3-PDO through Fed-Batch Fermentation Culture when Glucose and Glycerol are Added at Ratio of 1:3

Using the glucose/glycerol weight ratio selected in Example 3-1, fed-batch culture was performed to examine the 1,3-PDO production ability of the MBEL-HCC-C-13PDO1 strain.

First, the MBEL-HCC-C-13PDO1 strain was plated on a BHIS plate medium supplemented with kanamycin and spectinomycin and was cultured at 30° C. for 48 hours. The formed colony was inoculated into 50 mL of BHIS medium in the 250-mL Erlenmeyer flask having the cotton lid, selected in Example 2-3. Then, the colony was pre-cultured at 30° C. for 16 hours. The pre-culture was inoculated in 50 mL of CGXII medium ($OD_{600}$ at the start of culture=0.1) in each of four 250-mL baffle flasks (fermenter seed) and cultured in a shaking incubator at 200 rpm and at 30° C. for 24 hours. Here, the initial glycerol concentration of the CGXII medium was set to 40 g/L, 10 g/L of yeast extract was added to the medium, and MOPS was excluded. Thereafter, a total of 200 mL of the pre-culture was inoculated into 1.8 L of a CGXII fermentation medium (a fermenter with a total volume of 6 L) (start $OD_{600}$=3.0 to 4.0), glycerol was added at an initial glycerol concentration of 40 g/L, 10 g/L of yeast extract was added, and MOPS was excluded. In addition, each of $MgSO_4 \cdot 7H_2O$, biotin, thiamine, protocatechuic acid, kanamycin and spectinomycin was added after filtration. In addition, 1 mM IPTG was added at the first feeding at the end of the batch period.

During fed-batch fermentation culture, the pH was maintained at 7.0 using ammonia water (28%, Junsei Chemical Co., Ltd., Tokyo, Japan), and the temperature and the agitation speed were maintained at 30° C. and 600 rpm, respectively, in the P-I-D (proportional-integral-derivative) mode. The aeration rate was maintained at 0.25 vvm, and bubbles generated during culture were treated with antifoam 204 (Sigma-Aldrich). As feeding solutions, 800 g/L of glycerol solution and 800 g/L of glucose solution were prepared, and when the residual glycerol concentration decreased to 10 g/L, 50 mL of each of the solutions was added.

Figure 18:
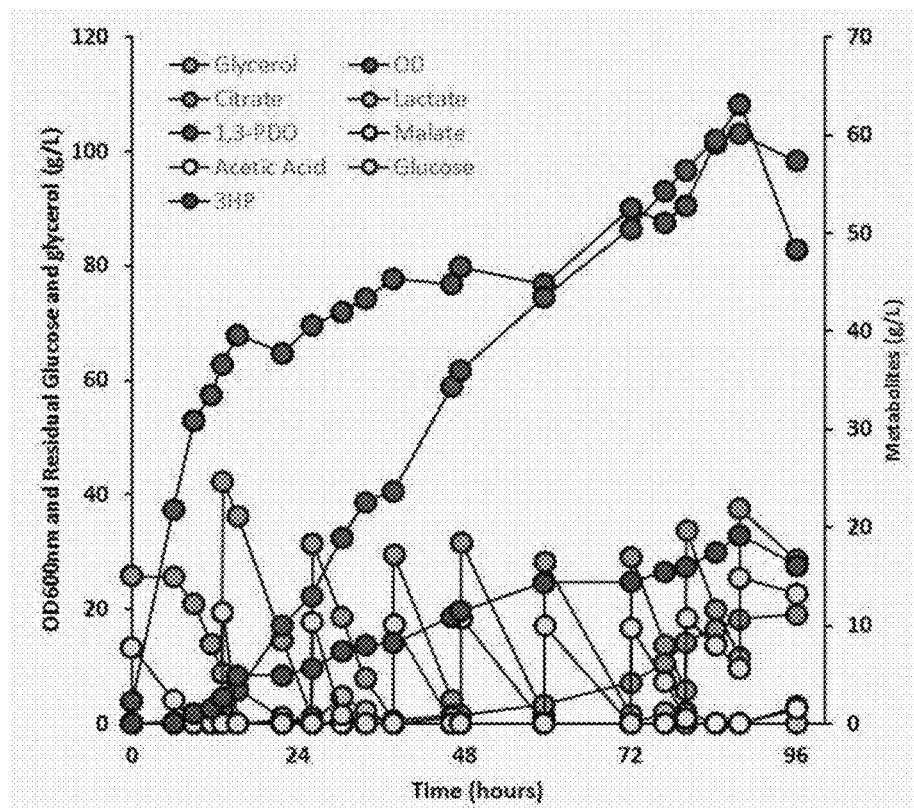
FIG. 18 shows the results of fed-batch fermentation culture of the MBEL-HCC-C-13PDO1 strain when glucose and glycerol are used at a weight ratio of 1:3.

As a result, as shown in FIG. 18, it could be confirmed that, when fed-batch fermentation culture of the MBEL-HCC-C-13PDO1 strain was performed using glucose and glycerol added at a weight ratio of 1:3, about 60.1 g/L of 1,3-PDO was produced. That is, it was confirmed that, when glucose and glycerol were added at a weight ratio of 1:3, the MBEL-HCC-C-13PDO1 strain more efficiently produced 1,3-PDO while cells grew.

3-3: Mutant Microorganism that Produces 1,3-PDO through Fed-Batch Fermentation Culture when Glucose and Glycerol are Added at Ratio of 1:2

In Example 3-2, the 1,3-PDO production ability of the MBEL-HCC-C-13PDO1 strain was confirmed through fed-batch culture after glucose and glycerol were added at a weight ratio of 1:3. However, it was confirmed that a large amount of 3-HP was still produced as a by-product. In order to apply the finding that 3-HP production decreased as the amount of glucose increased, as shown in Example 3-1, fed-batch fermentation culture of the MBEL-HCC-C-13PDO1 was performed using glucose and glycerol, added at a weight ratio of 1:2.

The fed-batch culture was performed in the same manner as in Example 3-2. As feeding solutions, 800 g/L of a glycerol solution, 800 g/L of a glucose solution, 200 g/L of a $MgSO_4 \cdot 7H_2O$ solution, and 200× TMS solution were prepared, and when the residual glycerol concentration decreased to 10 g/L, the solutions were added in amounts of 50 mL, 100 mL, 5 mL and 5 mL, respectively. The TMS solution composition used here is shown in Table 4 below.

TABLE 4

| Components of 200× TMS solution | |
|---|---|
| Components of TMS solution | Concentrations (200×) |
| $CaCl_2 \cdot 2H_2O$ | 2.6 g/L |
| $FeSO_{40} \cdot 7H_2O$ | 2.0 g/L |

TABLE 4-continued

| Components of 200× TMS solution | |
|---|---|
| Components of TMS solution | Concentrations (200×) |
| MnSO$_4$ · 5H$_2$O | 2.8 g/L |
| ZnSO$_4$ · 7H$_2$O | 0.2 g/L |
| CuSO$_4$ · 5H$_2$O | 0.06 g/L |
| NiCl$_2$ · 6H$_2$O | 4 mg/L |

Figure 19:
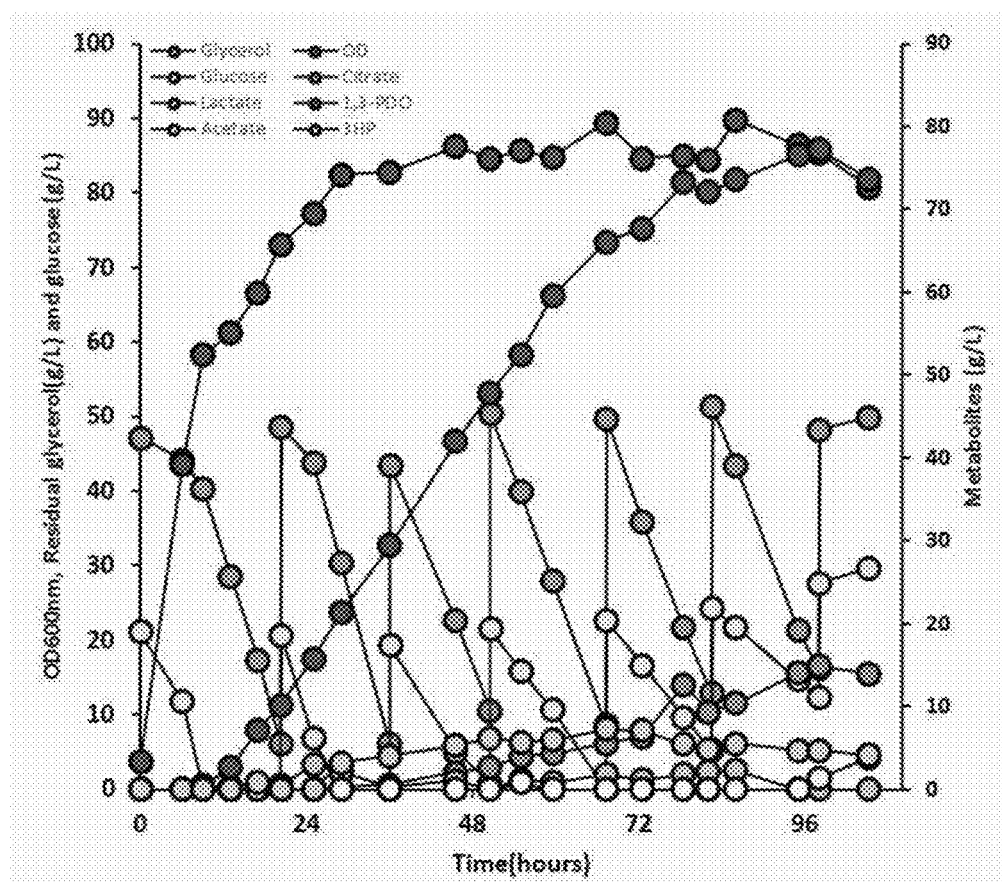
FIG. 19 shows the results of fed-batch fermentation culture of the MBEL-HCC-C-13PDO1 strain when glucose and glycerol are used at a weight ratio of 1:2.

As a result, as shown in FIG. 19, it was confirmed that, when fed-batch culture of the MBEL-HCC-C-13PDO1 strain was performed using glucose and glycerol added at a weight ratio of 1:2, about 77.5 g/L of 1,3-PDO was produced. In addition, it was confirmed that 3-HP production greatly decreased to about 7.2 g/L. That is, it was confirmed that, when glucose and glycerol were added at a weight ratio of 1:2, the MBEL-HCC-C-13PDO1 strain more efficiently produced 1,3-PDO while the cells grew.

INDUSTRIAL APPLICABILITY

According to the present disclosure, it is possible to produce 1,3-PDO while growing a mutant microorganism having 1,3-PDO production ability using the inexpensive raw material glycerol as a single carbon source. Thus, the present disclosure is useful for economical production of 1,3-PDO.

Although the present disclosure has been described in detail with reference to specific features, it will be apparent to those skilled in the art that this description is only of a preferred embodiment thereof, and does not limit the scope of the present disclosure. Thus, the substantial scope of the present disclosure will be defined by the appended claims and equivalents thereto.

Sequence List Free Text

An electronic file is attached.

The invention claimed is:

1. A method of producing 1,3-propanediol from glycerol, the method comprising steps of:
    (a) culturing a mutant microorganism, the mutant microorganism being a mutant of a microorganism *Corynebacterium glutamicum* spp., MBEL-HCC-C-13PDO1 deposited as KCTC Accession Number 15328BP, transformed with a glycerol facilitator-encoding gene glpF, a glycerol kinase-encoding gene glpK, a glycerol-3-phosphate dehydrogenase-encoding gene glpD, a glycerol dehydratase and glycerol reactivase encoding gene cluster pduCDEGH, and 1,3-PDO oxidoreductase-encoding gene yqhD, wherein the culturing is carried out in a glycerol- and glucose-containing medium, in which a weight ratio of the glucose to glycerol in the medium is 1:2 to 9, thereby producing 1,3-propanediol; and
    (b) collecting the produced 1,3-propanediol.

2. The method of claim 1, wherein a weight ratio of the glucose to glycerol in the medium is 1:2 to 3.

* * * * *

UNITED STATES PATENT AND TRADEMARK OFFICE
CERTIFICATE OF CORRECTION

PATENT NO. : 11,898,188 B2
APPLICATION NO. : 16/962213
DATED : February 13, 2024
INVENTOR(S) : Sang Yup Lee et al.

Page 1 of 1

It is certified that error appears in the above-identified patent and that said Letters Patent is hereby corrected as shown below:

In the Specification

Column 5, after Line 63 and before Line 64, the following paragraph should be inserted:
-- Therefore, in another aspect, the present disclosure is directed to a mutant microorganism in which a glycerol facilitator-encoding gene, a glycerol kinase-encoding gene, a glycerol-3-phosphate dehydrogenase-encoding gene, a glycerol dehydratase-encoding gene, a glycerol reactivase-encoding gene and a 1,3-propanediol oxidoreductase-encoding gene are introduced and which has the ability to produce 1,3-propanediol from glycerol. --

Column 6, Lines 1-4, the following paragraph should be deleted:
"In the present disclosure, the glycerol facilitator-encoding gene, the glycerol kinase-encoding gene and the glycerol dehydrogenase-encoding gene may be glpF, glpK and glpD, respectively."

Signed and Sealed this
Twenty-sixth Day of November, 2024

Katherine Kelly Vidal
*Director of the United States Patent and Trademark Office*